US012590003B2

(12) United States Patent
Awaja et al.

(10) Patent No.: US 12,590,003 B2
(45) Date of Patent: Mar. 31, 2026

(54) GRAPHENE OXIDE MATERIAL AND METHOD FOR THE PRODUCTION THEREOF

(71) Applicant: National University of Ireland, Galway, Galway (IE)

(72) Inventors: Firas Awaja, Galway (IE); Giorgio Speranza, Madrano (IT)

(73) Assignee: National University of Ireland, Galway, Galway (IE)

( * ) Notice: Subject to any disclaimer, the term of this patent is extended or adjusted under 35 U.S.C. 154(b) by 677 days.

(21) Appl. No.: 17/787,821

(22) PCT Filed: Dec. 17, 2020

(86) PCT No.: PCT/EP2020/086906
§ 371 (c)(1),
(2) Date: Jun. 21, 2022

(87) PCT Pub. No.: WO2021/123078
PCT Pub. Date: Jun. 24, 2021

(65) Prior Publication Data
US 2023/0035140 A1      Feb. 2, 2023

(30) Foreign Application Priority Data

Dec. 20, 2019    (EP) ..................................... 19218822

(51) Int. Cl.
| | |
|---|---|
| *C01B 32/198* | (2017.01) |
| *A61L 27/08* | (2006.01) |
| *C01B 32/194* | (2017.01) |
| *C01B 32/225* | (2017.01) |
| *H01M 4/36* | (2006.01) |
| *H01M 4/48* | (2010.01) |
| *H01M 4/02* | (2006.01) |

(52) U.S. Cl.
CPC ............ *C01B 32/198* (2017.08); *A61L 27/08* (2013.01); *C01B 32/194* (2017.08); *C01B 32/225* (2017.08); *H01M 4/366* (2013.01); *H01M 4/48* (2013.01); *C01B 2204/04* (2013.01); *C01B 2204/22* (2013.01); *C01P 2002/85* (2013.01); *C01P 2004/03* (2013.01); *H01M 2004/021* (2013.01); *H01M 2220/30* (2013.01)

(58) Field of Classification Search
CPC ... C01B 32/198; C01B 32/194; C01B 32/225; C01B 2204/04; C01B 2204/22; A61L 27/08; H01M 4/366; H01M 4/48; H01M 2004/021; H01M 2220/30; C01P 2002/85; C01P 2004/03
See application file for complete search history.

(56) References Cited

U.S. PATENT DOCUMENTS

| | | | | |
|---|---|---|---|---|
| 8,182,917 | B2 * | 5/2012 | Robinson | ............... B82Y 20/00 |
| | | | | 428/408 |
| 9,156,701 | B2 * | 10/2015 | Ho | ......................... C01B 32/192 |
| 2013/0130011 | A1 * | 5/2013 | Hong | .................... H10F 71/138 |
| | | | | 428/688 |
| 2015/0283555 | A1 | 10/2015 | Khe et al. | |
| 2018/0250704 | A1 | 9/2018 | Truica-Marasescu et al. | |
| 2019/0312267 | A1 | 10/2019 | He et al. | |
| 2019/0312276 | A1 | 10/2019 | He et al. | |

FOREIGN PATENT DOCUMENTS

| | | |
|---|---|---|
| CN | 107789668 A | 3/2018 |
| WO | WO-2009/085015 A1 | 7/2009 |
| WO | WO-2018/146592 A1 | 8/2018 |
| WO | WO-2019/106344 A1 | 6/2019 |

OTHER PUBLICATIONS

Baraket et al. Reduction of graphene oxide by electron beam generated plasmas produced in methane/argon mixtures, Carbon, vol. 48, Issue 12, 2010, 3382-3390, https://doi.org/10.1016/j.carbon.2010.05.031. (Year: 2010).*
Xu, Y.; Cao, H.; Xue, Y.; Li, B.; Cai, W. Liquid-Phase Exfoliation of Graphene: An Overview on Exfoliation Media, Techniques, and Challenges. Nanomaterials 2018, 8, 942. https://doi.org/10.3390/nano8110942 (Year: 2018).*
Compton et al. Tuning the Mechanical Properties of Graphene Oxide Paper and Its Associated Polymer Nanocomposites by Controlling Cooperative Intersheet Hydrogen Bonding, ACS Nano 2012, 6, 3, 2008-2019, https://doi.org/10.1021/nn202928w (Year: 2012).*
Jernigan et al. Physical properties of nanometer graphene oxide films partially and fully reduced by annealing in ultra-high vacuum. J. Appl. Phys. Aug. 21, 2017; 122 (7): 075301. https://doi.org/10.1063/1.4998812 (Year: 2017).*

* cited by examiner

*Primary Examiner* — Frederick F Krass
*Assistant Examiner* — Ashlee E Wertz
(74) *Attorney, Agent, or Firm* — Morse, Barnes-Brown & Pendleton, P.C.; Martin Z. Zhang; Russell L. Widom

(57) ABSTRACT

A method of producing a multi-layered functionalised graphene oxide paper, comprises the steps of providing an aqueous suspension of oxidised graphene oxide flakes, size reducing the oxidised graphene oxide flakes in the suspension to provide an aqueous suspension of particulate oxidised graphene oxide having an average particle size of less than 1 μm and drying the aqueous suspension in a vessel to provide a multi-layered graphene oxide material. The multi-layered graphene oxide material is annealed to provide a multi-layered reduced graphene oxide material, before surface grafting functional groups to the surface of the multi-layered reduced graphene oxide material by reacting the material with a functional group precursor in the presence of plasma. The use of a graphene oxide material to treat bone defects, and as an energy storage device, is also described.

16 Claims, 18 Drawing Sheets

(A)

(B)

(C)

survey

<u>Figure 8</u>

Inflammation

Bone production

Bone remodeling

GRAPHENE OXIDE MATERIAL AND METHOD FOR THE PRODUCTION THEREOF

CROSS-REFERENCE TO RELATED APPLICATIONS

This application is the National Stage of International Application No. PCT/EP2020/086906, filed on Dec. 17, 2020, which claims priority to EP application Ser. No. 19218822.5, filed on Dec. 20, 2019. The contents of both applications are hereby incorporated by reference in their entirety.

FIELD OF THE INVENTION

The present invention relates to a graphene oxide material, methods for producing the graphene oxide material, and uses of the graphene oxide material.

BACKGROUND TO THE INVENTION

Current treatment of complex fractures and bone healing is suboptimal at present, creating significant economic burden and reduced quality of life. The gold standard for treatment of fractures and bone healing is bone grafting through harvesting of host bone. Reliable, consistent bone samples are required to improve the likelihood of host adoption and bone regeneration. Currently, the prevalence of unsatisfactory repairs using autografts is as high as 30% and treatment and rehabilitation are both expensive and time consuming. Instrument offerings also present challenges which need to be overcome. Therefore, a need exists for more effective treatment to be created.

The unmet need to improve first time efficacy bone regeneration has been qualified following extensive discussions with numerous global clinical and industry Key Opinion Leaders including Prof. Michael Nogler and Prof. Martin Krissmer. The need has been further validated through comprehensive secondary industry analysis and peer reviewed clinical papers recommending a more efficacious and cost-effective treatment to be created for bone regeneration to improve healing times, first time efficacy and reduce global economic healthcare burden. Graphene has been proven recently to show faster, more efficacious and permanent bone healing in animal models. Graphene materials have strong potential to provide mechanisms for achieving spontaneous stem cell differentiation. Spontaneous cell differentiation means that the stem cells that are responsible for tissue regeneration and repair will be able to do so without the need to add toxic growth factor chemicals. The use of growth factor with stem cells shown to lead to the appearance of tumors and increase the risk for the degeneration in malignant tissue generation. Avoiding the use of these proteins or steroid hormones is thus an objective of the present invention. Achieving spontaneous differentiation in vivo means that clinical therapies for acute trauma injuries like strokes and spinal cord damage and age related cardiovascular, metabolic and neurodegenerative diseases could have efficient and permanent cure.

WO2019/106344 describes a method of providing a graphene oxide coating on a substrate such as a polymer comprising providing an aqueous suspension of particulate oxidised graphene oxide having an average particle size of less than 1 μm, drying the aqueous suspension in a vessel to provide a multi-layered graphene oxide material, and surface grafting functional groups to the surface of the multilayered graphene oxide material by reacting the material with a functional group precursor in the presence of plasma. The resultant material is described as having utility as a filtration membrane, especially for filtration of water. A problem with the graphene oxide coating of this method is that the graphene oxide is unstable and liable to be released as free radicals that pose a serious health problem, especially in the context of water filtration.

It is an object of the invention to overcome at least one of the above-referenced problems.

SUMMARY OF THE INVENTION

The Applicant has addressed the problems of the prior art by annealing the multi-layered graphene oxide material prior to surface grafting to reduce the graphene oxide material, and then applying a plasma treatment to the reduced graphene oxide material in the presence of an alkane. The annealing step reduces the relative oxygen concentration in the graphene oxide material, typically from about 50% to about 10-25%, and also crosslinks the graphene oxide flakes. Treating the reduced graphene oxide material in plasma in the presence of an alkane further crosslinks the graphene oxide flakes to increase the material stability and resistance to water, chemicals and mechanical stress, reduces the relative oxygen concentration further (for example to about 5%), and fills voids on the surface by deposition of an amorphous carbon substance, reducing the surface roughness to a micron scale which allows cells to better adhere to the surface during use. The annealing process dictates the connections between monolayers. Plasma treatment ensures that there is a chemical link through covalent bonding between the layers both horizontally and vertically to ensure integrity, stability and functionality. This multilayered structure provides the material with good mechanical properties to be handled and cut following the desired shapes and utilized as a stable substrate for cell adhesion assays.

The invention provides a modified graphene oxide thin sheet material (graphene (GO) paper), typically having more than 50 or 100 sheets, that generally has a micron-sized thickness and that can cause spontaneous differentiation of stem cells into osteoblasts in the absence of growth factors. The material is produced by exfoliating crystalline graphite in strong acid to produce a suspension of highly oxidised graphene oxide flakes, size reduction of the suspension to provide a homogenous suspension of graphene oxide, drying of the suspension to produce a solid multi-layer structure, and then annealing of the structure to provide a network of covalent linkages between adjacent layers. The material may then be treated in non-thermal plasma to surface graft a discontinuous film of functional groups on to the surface, for example methane and amine groups, which stabilise the graphene surface and at the same time provide functionalities (for example hydroxyl, amine or carboxy) for cell adhesion, without fully masking the underlying graphene oxide. The resultant material has a surface roughness on a micron scale, which promotes the adhesion of cells to the surface, and incorporates intra-layer and inter-layer covalent bonds that provide integrity, stability and functionality. The carbon and oxygen content of the material may be tuned to match specific tissue (for example bone), and the stiffness may be varied over a range of 20 GPa to 40 GPa by varying the residual water content of the material after drying and annealing. Surface grafting of functional groups may be varied to optimise the surface for the adhesion of various cell types.

In a first aspect, the invention provides a method of producing a multi-layered graphene oxide material, comprising the steps of:

providing an aqueous suspension of graphene oxide, typically oxidised graphene oxide, flakes;

size reducing the graphene oxide flakes in the suspension to provide an aqueous suspension of particulate graphene oxide having an average particle size of less than 1 μm;

drying the aqueous suspension in a vessel to provide a multi-layered graphene oxide material; and annealing the multi-layered graphene oxide material to provide a multi-layered reduced graphene oxide material.

In one embodiment, the method comprises surface grafting functional groups to the surface of the multi-layered reduced graphene oxide material by reacting the material with a functional group precursor in a reactor in the presence of plasma. This provides a stand-alone graphene oxide sheet/paper.

In one embodiment, the drying step is configured to provide the multi-layered reduced graphene oxide material as a thin sheet, for example having a thickness of less than 3000, 1000, 500, 400, 300, 200, 100, 50, 20, 10, 5, or 1 μm. In one embodiment, the material has a thickness of less than 2 μm, and typically about 1 μ. In one embodiment, the material has a thickness of 1-3000, 1-1000, 1-500, 1-400, 1-300, 1-200, 1-100, 1-50, 1-20, 1-10 or 1-5 μm. In one embodiment the material comprises at least 10, 20, 30, 40, 50, 100, 150, 200, 300, 400 or 500 layers.

In one embodiment, the multi-layered reduced graphene material has a relative oxygen concentration of 10-25%.

In one embodiment, the multi-layered graphene oxide paper produced according to the method of the invention has a relative oxygen concentration of less than 10%, 8%, 6%, or about 4-6%.

In one embodiment, the annealing step is configured to crosslink graphene oxide flakes to the effect of 60-70 interlock.

In one embodiment, the functional group precursors are selected from a group consisting of an alkane, amine, oxygen and hydrogen. Examples of alkanes include methane, ethane and propane. In one embodiment, the amine is ammonium. Other amines include other primary amines, and second and tertiary amines.

In one embodiment, the functional group precursor is selected from (a) an alkane and an amine (preferably methane and ammonia), or (b) an alkane and oxygen. Generally the alkane is added first, and then the second functional group (e.g. an amine, hydrogen or oxygen) is then added.

In one embodiment, the functional group precursor is provided to the plasma reactor at a flow rate of 10-100, 10-50, or 20-40 sccm. In one embodiment, an alkane and amine precursor are employed. In one embodiment, the flow rates of the alkane and amine are varied from 10:1 to 1:10, preferably 4:1 to 1:4. In one embodiment, the flow rates of the alkane and amine are as provided in Table 1 below.

In one embodiment, the pressure in the plasma reactor is less than 0.1 mbar, 0.05 mbar, and ideally less than 0.02 mbar.

In one embodiment, the reactor is configured to provide a plasma with an ion density of greater than 500/cm³, 750/cm³ or 1000/cm³.

In one embodiment, the plasma is non-thermal plasma. In one embodiment, the plasma is low-pressure plasma. In one embodiment, the plasma is plasma afterglow (glow discharge).

In one embodiment, the suspension of oxidised graphene oxide flakes is obtained by exfoliation of crystalline graphite in a strong acid solution (i.e. produced by the Hummer process or a modified Hummer process). Generally the acid is concentrated sulphuric acid.

In one embodiment, the oxidised graphene oxide flakes in the suspension are size reduced by a process of sonication.

In one embodiment, the aqueous suspension employed in the drying step has a concentration of particulate graphene oxide of about 1-100 mg/ml, 1-10 mg/ml, typically about 3-5 mg/ml, and ideally about 4 mg/ml.

In one embodiment, the annealing step is performed at a temperature of 150-850° C., 150-500° C., 150-300° C., 150-250° C., preferably about 190-201 ° C., and ideally about 200 ° C. In one embodiment, the material is annealed for 1-5 hours, preferably about 3 hours. It will be appreciated that the annealing time and temperature may be varied and that higher temperatures may be employed with shorter times and vica-versa.

In one embodiment, the drying and annealing steps are configured to provide multi-layered reduced graphene oxide material having a stiffness of about 20-40 GPa, ideally about 20-25 GPa.

The Applicant has also discovered that the multi-layered graphene oxide material of the invention exhibit high energy storage and specific fast charging and discharging properties, and as such are suitable for use as energy storage devices (i.e. batteries). For the energy storage application, the process may be optimised. Thus, in one embodiment, the process employs higher drying and annealing temperature than described above. In one embodiment, two plasma treatments are performed, a first with methane and hydrogen precursors, and a second with hydrogen precursor.

The invention also provides a multi-layered graphene oxide material obtainable by a method of the invention.

The invention also provides a multi-layered graphene oxide material having a multiplicity of graphene oxide layers including external layers and intermediate layers sandwiched between the external layers, in which adjacent layers are linked by means of covalent bonding. Typically the material is a graphene oxide (GO) paper.

In one embodiment, the exposed surface of the external sheets comprises a discontinuous thin film of surface grafted functional groups.

In one embodiment, the multi-layered graphene oxide material is provided as a provided as a thin sheet.

In one embodiment, the graphene oxide layers, in particular the intermediate graphene oxide layers, comprise about 83.5% carbon and 16.5% oxygen.

In one embodiment, the surface of the sheet has a micro-scale roughness.

In one embodiment, the sheet is flexible.

In one embodiment, the surface grafted functional groups are selected from the group consisting of an alkane, amine, oxygen and hydrogen.

In one embodiment, the surface grafted functional group is selected from (a) an alkane and an amine, or (b) an alkane and oxygen.

In one embodiment, multi-layered graphene oxide material has a stiffness of about 20-40 GPa.

In one embodiment, the multi-layered graphene oxide material a stiffness of about 20-25 GPa.

In one embodiment, the thin film of surface grafted functional groups comprises about 1% to about 3% oxygen.

In one embodiment, the thin film of surface grafted functional groups comprises about 5% to about 25% oxygen (relative oxygen concentration).

In one embodiment, the multi-layered graphene oxide material is infused with stem cells. In one embodiment, the stem cells are derived from adipose or bone barrow tissue.

In another aspect, the invention provides an energy storage device comprising a multi-layered graphene oxide material of the invention. The energy storage device may be for example a battery, fuel cell, capacitor, or a supercapacitor. In one embodiment, the energy storage device is a battery for a mobile device such as a phone.

The invention also provides a multi-layered graphene oxide material according to the invention, for use in a method of treating a bone in a mammal to regenerate bone tissue, in which the graphene oxide material is administered to the bone. In one embodiment, stem cells are also administered to the bone, in which the multi-layered graphene oxide material causes in-vivo spontaneous differentiation of the stem cells.

The invention also provides a method of treating a bone in a mammal to effect regeneration of bone, the method comprising a step of administering a multi-layered graphene oxide material of the invention to the bone. In one embodiment, stem cells are also administered to the bone, in which the multi-layered graphene oxide material causes in-vivo spontaneous differentiation of the stem cells.

In one embodiment, the bone has a bone defect, and the multi-layered graphene oxide material is administered to the bone defect, for example covering or filling-in the bone defect.

In one embodiment, stem cells are also administered to the bone defect, in which the graphene oxide material causes in-vivo spontaneous differentiation of the stem cells.

In one embodiment, the multi-layered graphene oxide material is provided as a sheet.

In one embodiment, the sheet of multi-layered graphene oxide material is placed over the bone defect.

The invention also provides a multi-layered graphene oxide material according to the invention, for use as an energy storage material in an energy storage device.

The invention also provides an energy storage device comprising as an energy storage material a multi-layered graphene oxide material according to the invention.

Other aspects and preferred embodiments of the invention are defined and described in the other claims set out below.

a.: (t=0, implantation) CS Defect in rat calvaria treated with test biomaterials (GO, O-GO, N-GO sheets)

b.: (intermediate t) bone regeneration started from the edges of the calvarial defect, supported by GO sheet c.: (t=8 weeks after implantation) consistent crown-shaped bone regeneration has formed.

FIG. 13A-D: Old bone (A) connectivity and (B) BV (mm3) and New bone (C) BV/TV and (D) connectivity.

Figure 14A:
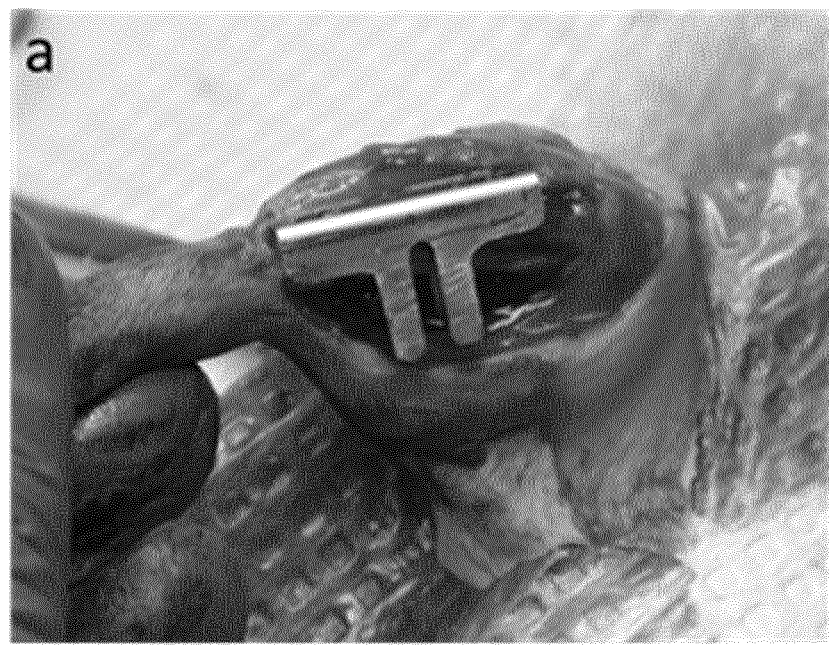
Figure 14B:
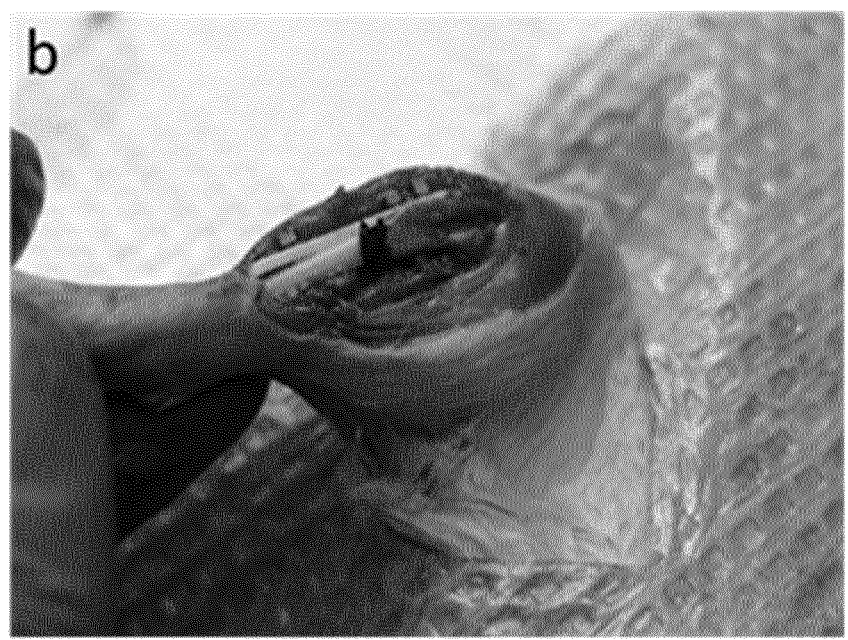
Figure 15:
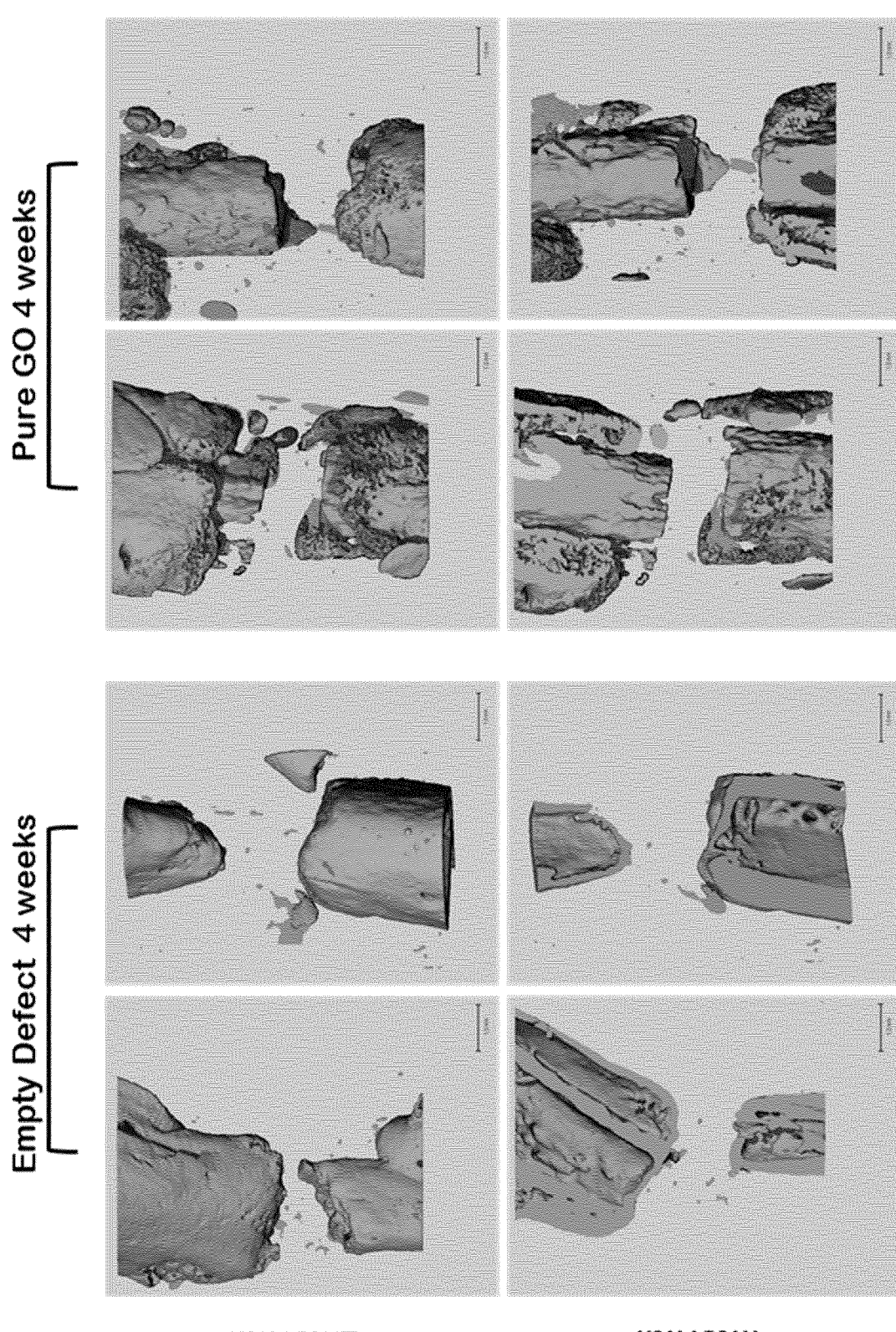
Figure 16:
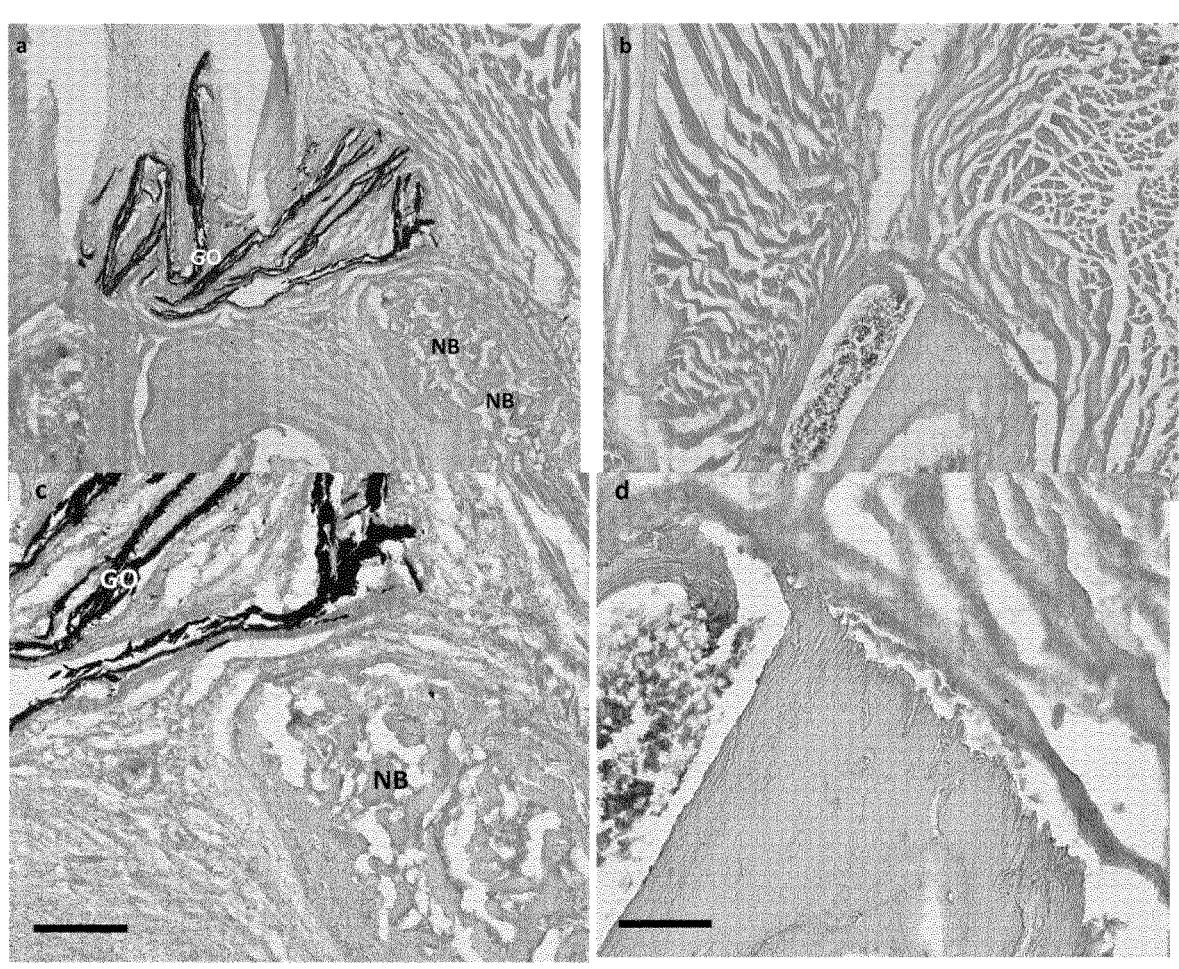

FIG. 14A-14B: Tibia surgery with (A) control and (B) modified GO implantation FIG. 15: CT scans that shows new bone (in red) for (left) control and (right) modified GO FIG. 16: Representative Histological cross sections of pure graphene oxide and empty controls from tibiae explanted after 4 weeks. (b) The empty-defects controls were primarily filled with loose connective tissues filling the defect. Scale bar=500 nm. (a) Pure GO specimens show new bone formation (NB). Scale bar=500. (c,d) Magnification of c & d respectively. Scale bar=200 nm.

Figure 17:
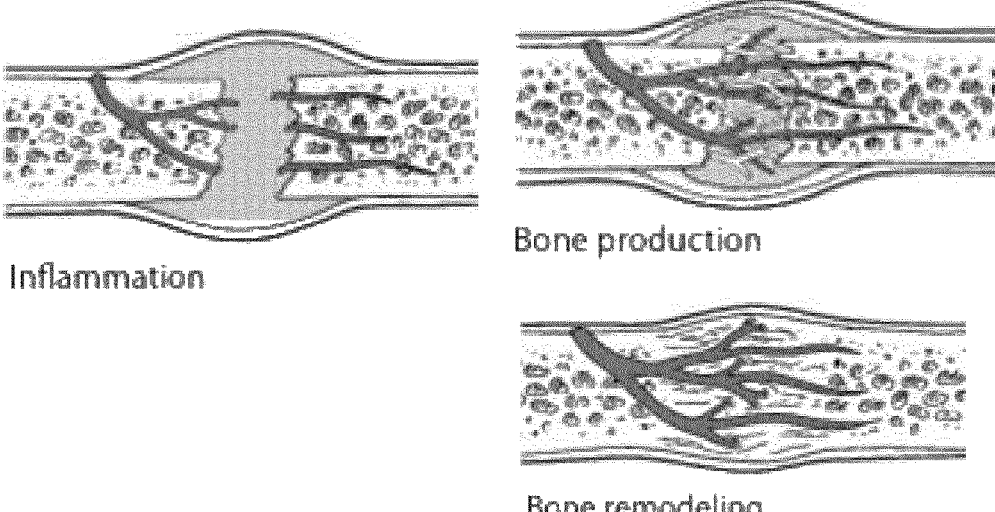

FIG. 17: Schematic of bone healing mechanism.

Figure 18:
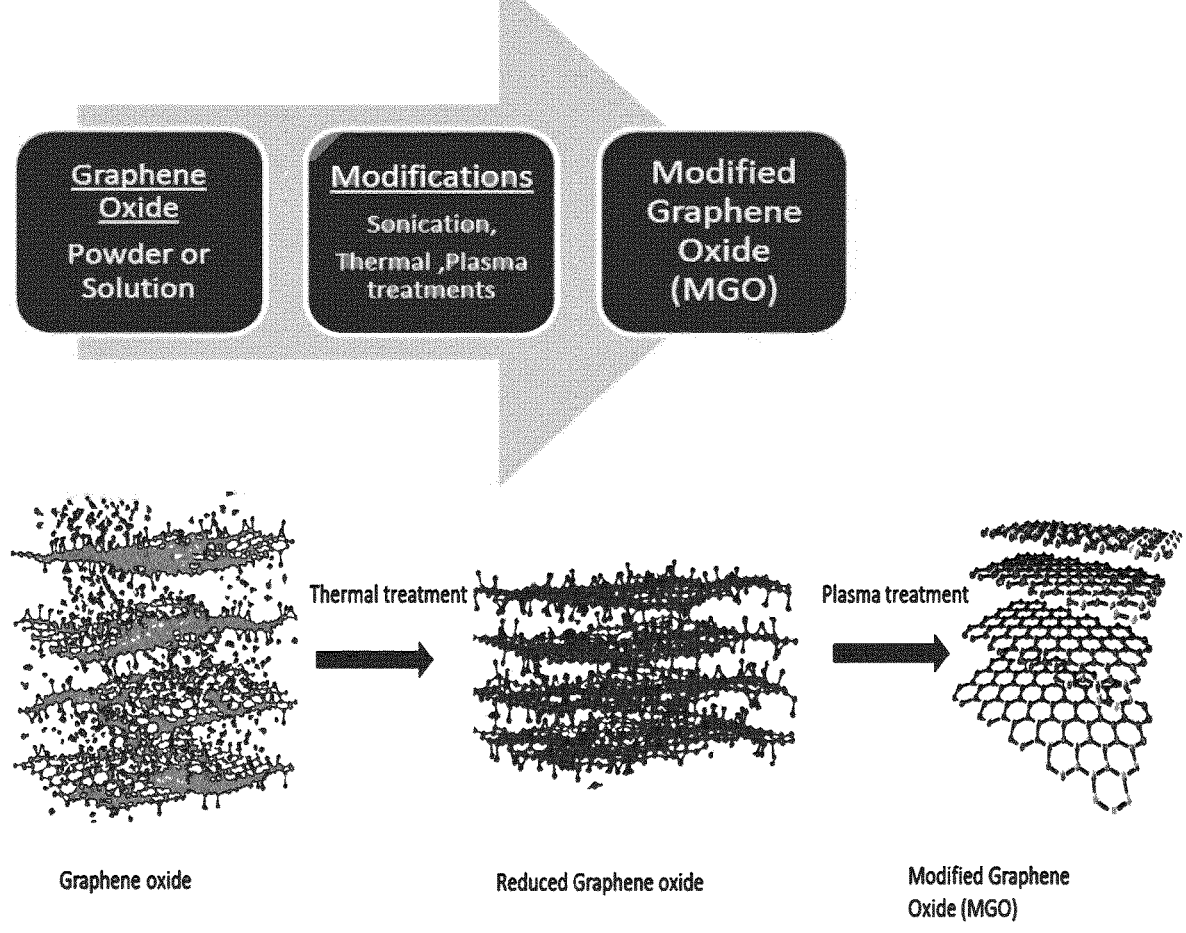

FIG. 18: Energy storage application: schematic process (top) and associated structural changes (bottom)

Figure 19A:
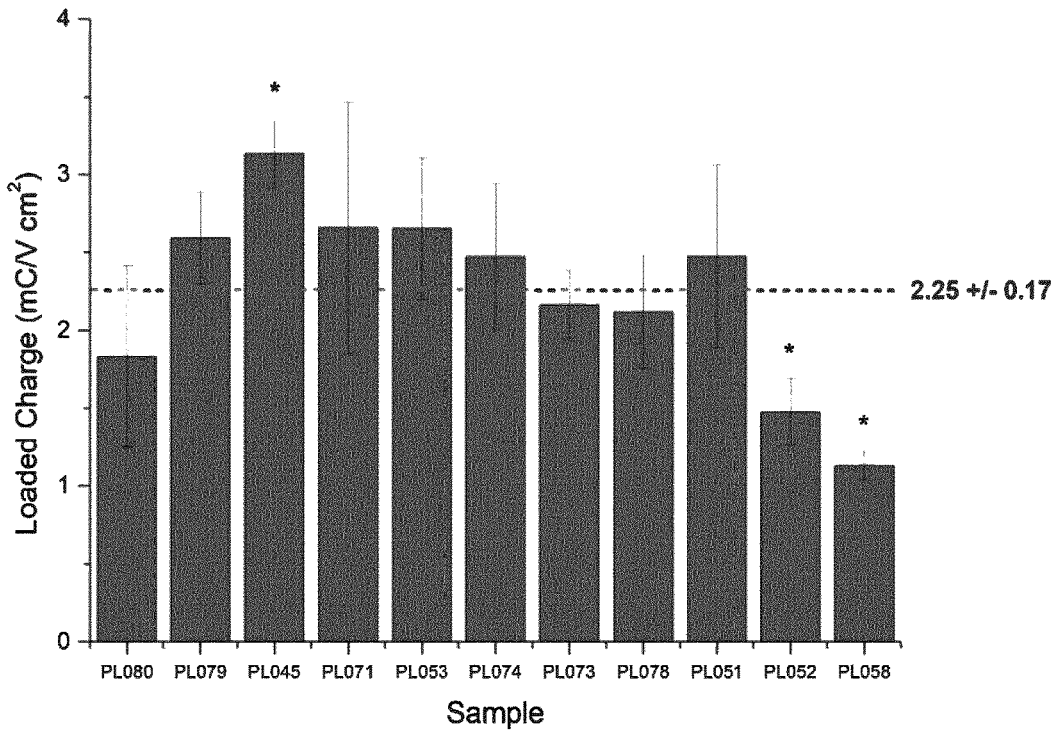
Figure 19B:
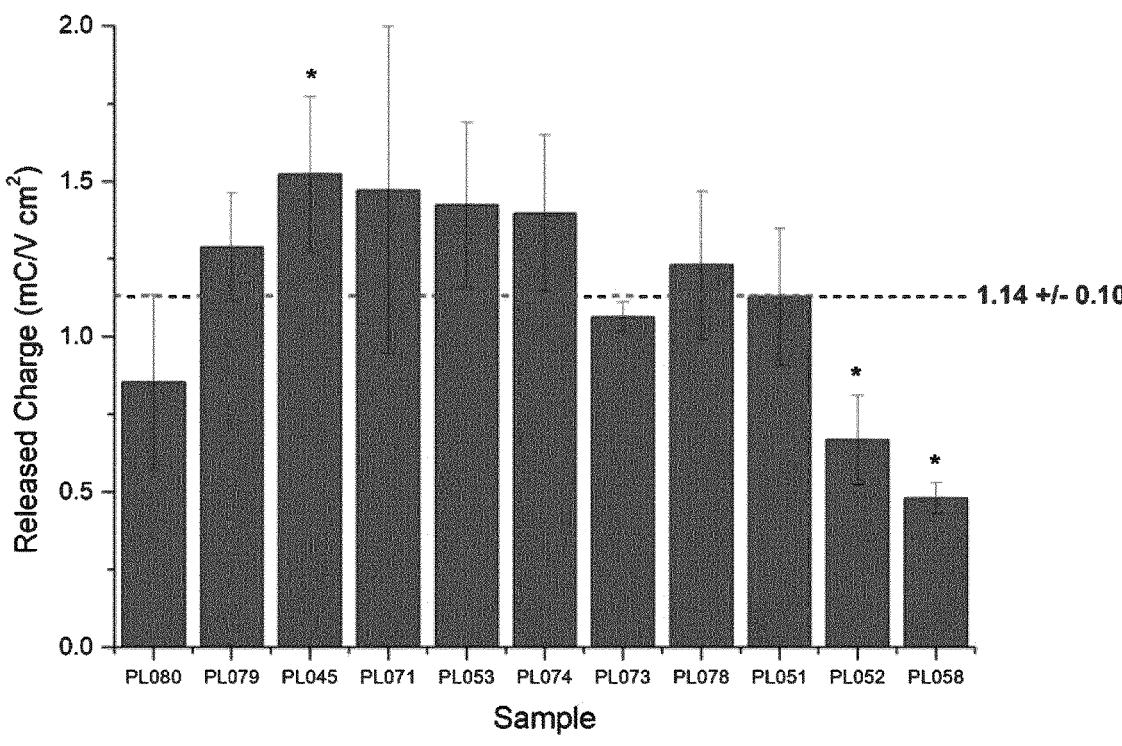

FIG. 19: Average values of charge loaded (A) and released (B), in 80 seconds FIG. 20: Specific energy and specific power of the graphene oxide material of the invention (MGO) as compared to capacitors, supercapacitors, batteries, and fuel cells.

DETAILED DESCRIPTION OF THE INVENTION

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, age, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure. Improvement may be observed in biological/molecular markers, clinical or observational improvements. In a preferred embodiment, the methods of the invention are applicable to humans, large racing animals (horses, camels, dogs), and domestic companion animals (cats and dogs).

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, camels, bison, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human. As used herein, the term "equine" refers to mammals of the family Equidae, which includes horses, donkeys, assess, kiang and zebra.

"Oxidised graphene oxide flakes" refers to graphene oxide that is prepared usually from graphite and is provided in the form of a suspension of graphene oxide flakes which are oxidised. Graphene oxide flakes may be prepared by a chemical process such as exfoliation of crystalline graphite in a strong acid solution (e.g. Hummer or modified Hummer method), by electrochemical exfoliation of graphite, or by oxidation methods. Hummer methods are described in Hummers et al (Journal of the American Chemical Society. 80 (6): 1339. doi:10.1021/ja01539a017), Procedia Engineering 184 (2017) 469 — 477, and Scientific Reports volume 6, Article number: 36143 (2016). Electrochemical exfoliation of graphite is described in J. Mater. Chem. A, 2014,2, 15428-15436 and Carbon Energy. 2019;1:173-199. Other method of producing oxidised graphene oxide flakes are water electrolytic oxidation methods (e.g. NATURE COMMUNICATIONS 1 (2018) 9:145) and use of preformed acidic oxidizing medium (Scientific Reports |7: 3908| DOI:10.1038/s41598-017-04139-0). The Hummer method provides highly oxidised graphene oxide flakes. The chemical composition of oxidised graphene oxide flakes produced according to the Hummer method is generally about Carbon: 49-56%, Hydrogen: 0-1%, Nitrogen: 0-1%, Sulfur: 0-2%, and Oxygen: 41-50%. Typically about 30%, 40% or 50% of the carbon atoms in the flakes are in an oxidized from.

"Size reducing" as applied to the graphene oxide flakes refers to a treatment to reduce the size of the flakes to an average particle size of less than 1 μm. Methods of size reducing flakes of material to the specified size will be apparent to a person skilled in the art and include sociation (described below), wet milling and high-pressure homogenisation. Wet ball milling is described in Zhao et al (J. Mater Chem. 2010, 20, 5817-5819). High Pressure Homogenisation is described in Qi et al. (ACS Appl Mater Interfaces. 2017 Mar 29;9(12)11025-11034.)

"Drying" refers to a process of removing water from the suspension of oxidised graphene oxide particulates to provide a solid sheet. The thickness of the sheet is generally on the micron scale (e.g. 1-1000 microns). The drying may be performed by any method which removes water from the suspension to provide a solid sheet. In the embodiments described herein, the suspension is dried in a petri dish at room temperature, although other drying methods could be employed. Drying prior to annealing prevents hydrolysis and cracking reactions in the annealed graphene oxide.

"Annealing" refers to a process in which the sheet produced in the drying step is heat-treated at an elevated temperature to remove residual water and stabilise the material. The temperature and time employed for the annealing step may be varied, for example 150-250° C. for 1-5 hours may be employed, although higher temperatures may be employed as well. Generally, the drying and annealing steps are configured to provide a sheet with a stiffness of 20-40 GPa, which is suitable for use with bone.

"Functional groups" refers to atoms or molecules that are grafted to the surface of the material during the final plasma step that affect the functionality of the surface of the material. Examples include carboxyl (COOH), hydroxyl (OH) and amine groups. The functional groups are derived from functional group precursors that are introduced into the plasma. The functional group precursors may be selected from an alkane (e.g. methane), an amine (e.g. ammonia), $O_2$, and $H_2$. An alkane functional group precursor such as methane is generally added to the plasma to deposit an amorphous carbon substance in the voids on the surface, reducing the roughness of the surface and improving its anti-biofilm functionality. The macroscopic polarity of the substrate surface is the result of the interplay between the negative oxygen based polar groups (mainly COOH— and OH— groups) belonging to the GOP surface and the positively charged amine groups NH3+. A careful selection of the precursor mixture allows controlling the density of the grafted functionalities. This allows surface conditioning to promote cell adhesion while, at the same time, avoiding ECM protein denaturation. For example, the amount of OH or COOH groups on the surface of GO can be modified through changing the precursor (e.g. H2, $O_2$, $CH_4$) of the plasma treatment and in some cases the bombardment energy in the plasma treatment step, where $H_2$ treatment can increase OH functional groups and $O_2$ can increase COOH functional group density on the surface.

"Non-thermal low pressure plasma" should be understood to mean a plasma assisted chemical vapour deposition process conducted in low pressure (vacuum pressure) and not atmospheric, and that the process does not require a heating source and is conducted in room temperature. "Relative oxygen concentration" as applied to a material means the number of atoms of oxygen relative to the total number of atoms present on the surface. It is measured using an instrument called X-ray Photoelectron Spectroscopy (XPS).

Exemplification

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

The invention regards the synthesis of a multilayered coating for cell adhesion and proliferation and tissue regeneration and repair. The material synthesis is composed by three steps: 1) manufacture of the of a multilayered GO based substrate; 2) controlled annealing and reduction of the GO to produce self-standing GO substrates (GO-paper); 3) deposition of a second coating aimed at stabilizing, functionalizing strengthening the GO substrate to make it a favourable platform for stem cell proliferation and growth for tissue regeneration and repair.

Synthesis of the Multilayered Substrate

The Graphene Oxide is obtained from exfoliation of crystalline graphite through a chemical processing in a strong acid solution (hummer process). The exfoliation process leads to a solution of strongly oxidized graphene flakes. Originally the graphene is composed by a single layer of carbon atoms arranged in a hexagonal crystalline lattice. The graphene monolayer is a 2D material characterized by an outstanding specific surface. The exfoliation process of graphite leads to the formation of a population of particulate where the mean flake dimension ranges from sub nanometer scale to up to ~30 μm. 95% of the flakes are in the form of monolayers. However, differently from the pure ideal graphene, the graphene oxide appears to be strongly oxidized. The chemical composition of GO is Carbon: 49-56%, Hydrogen: 0-1%, Nitrogen: 0-1%, Sulfur: 0-2%, Oxygen: 41-50% where about the half of the carbon atoms are in an oxidized from. The graphene oxide is in the form of an aqueous solution at a pH of 2.2, 2.5 and a concentration of 4 mg/ml.

A sonication process is then employed, thereafter, to grind down the larger particles to have a uniform particles size less than 1 μm. This will ensure homogeneity and represent a basic layer that has less roughness and more potential for producing films or membranes with higher conductivity.

Figure 1:
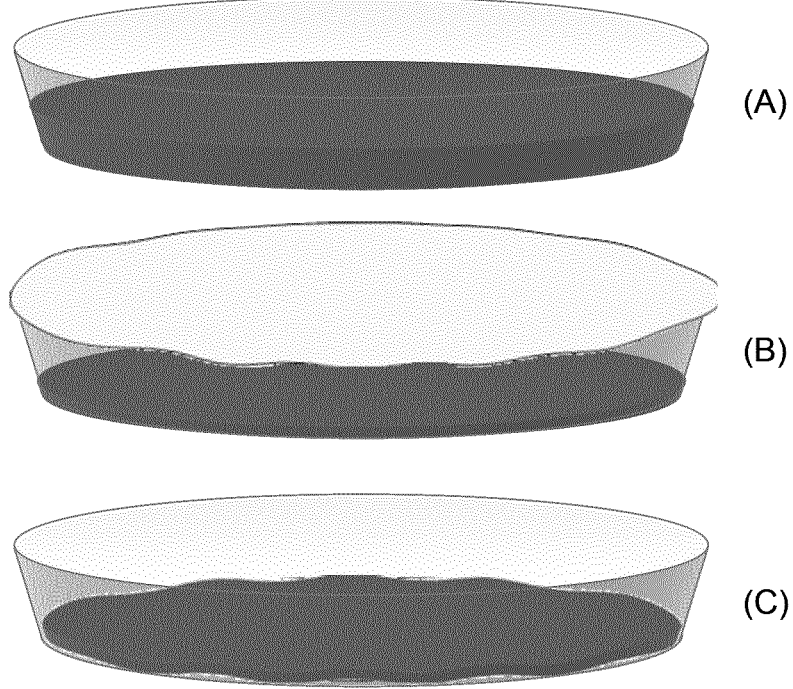
FIG. 1: Synthesis of the GO multilayered substrate that are free from cracks, microcracks and ripples. With the right water content and oxygen functionalities. GO solution is placed in a glassy petri (A) and let dry for 48 hours (B). The petri is then put in an oven at 200° C. for 3 hours. As a result, the GO film detaches from the glass bottom and make possible to remove it from the petri.

The multi-layered GO based substrate is synthesized by placing 25 ml of a water suspension of graphene oxide at a concentration of 4 mg/ml, in a 7 cm diameter glass petri (see FIG. 1). The suspension was sonicated for 1-2 h at 40-50° C. The suspension was allowed to dry at room temperature by placing a filter papers on the petri to avoid contamination of the underlying GO. After 48 hours drying, the Petri were introduced in an oven and the temperature slowly increased (according to a temperature program and up to 200° C. for 3hours). The dried GO is then placed in an oven at 200° C. to desorb the residual water and stabilize the multilayer structure. This last treatment causes the GO coating to detach from the glass petri and allow simple removal with tweezers.

The substrates are then detached form the petri and introduced in the plasma reactor for further surface treatment. The stiffness of the material can be tuned on the basis of the water content which is present among the layers of the GO substrate. In particular it has been demonstrated that it can be varied between 20 GPa and 40 Gpa. For this invention, the water content in the synthesised films were kept at a level that result in materials stiffness close to 20 GPa which is suitable for bone tissue growth. The process of detachment of these thin films from the annealing containers depends largely on variables such as the water content, thickness and homogeneity of the films. The homogeneity of the films in turn depends on the initial particles size and distribution.

Figure 2:
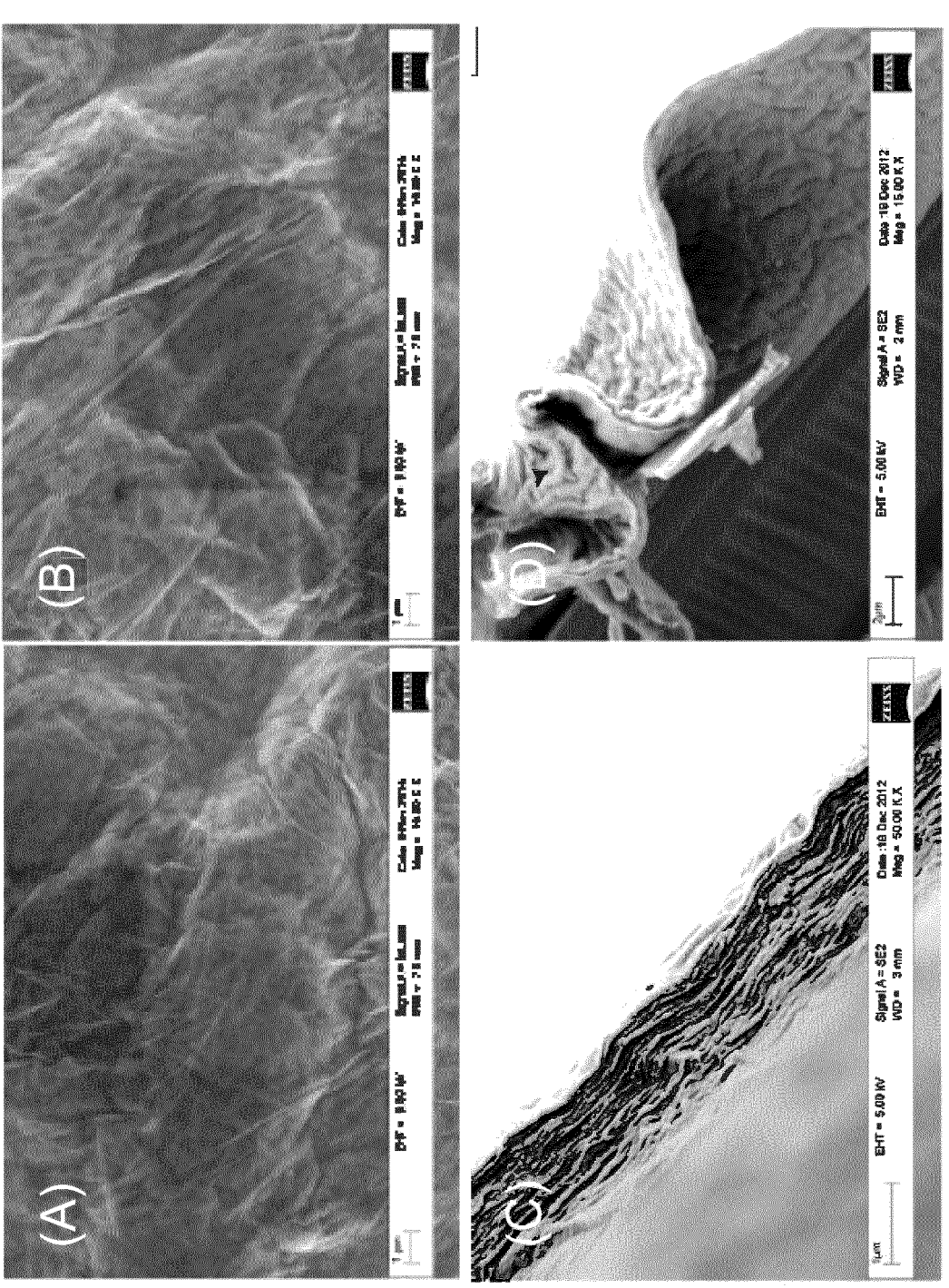
FIG. 2: SEM images of the GO paper: superficial corrugation (A) and (B), section showing the multilayered structure (C), flexibility of the GO paper (D).

In FIG. 2 are shown SEM images of the multilayered substrate which is synthesized following the procedure described above. It is important to observe the superficial corrugation of the GO sheet, the roughness is on the micron scale as desired by cells to better adhere to a surface. The annealing process dictates the samples roughness and the connections between monolayers. Plasma treatment ensures that there is a chemical link through covalent bonding between the layers both horizontally and vertically to ensure integrity, stability and functionality.

In FIG. 2C it is shown a section of the material where the multilayered structure appears. This multilayered structure provide the material with good mechanical properties to be handled and cut following the desired shapes and utilized as a stable substrate for cell adhesion assays.

Plasma Reactor

The plasma reactor is generally designed to perform low pressure plasma discharges. The reactor is formed by a load-lock chamber to introduce the medical device into the plasma chamber for treatment. The load lock chamber is pumped down from atmospheric pressure till to 10-6 mbar. The evacuation of the load-lock chamber ensures a negligible degree of contaminants to enter in the plasma chamber with the introduction of the objects to be treated. The plasma chamber consists of a rather big stainless teal ellipsoidal chamber with a diameter of –500mm to avoid interferences of the chamber walls during the plasma treatment. The plasma chamber is equipped with a plasma source which is a commercial COPRA GTE 200 plasma source (from CCR Technology GmbH-Germany). The source is equipped with an inner matching network to couple the external RF generator, minimize the reflected RF power and optimizing the transfer of the RF power to the plasma. The plasma source is also equipped with a magnetic coil. A maximum RF power is transferred to the plasma when the magnetic field is tuned to form a wave resonance (cyclotron resonance) leading to a strong increase of the ionization processes. In this configuration the plasma is generated inside the plasma source and propagated outside through the source output till to the sample surface. The samples are then exposed to an afterglow high density plasma but reasonably low power avoiding heat transfer during the depositions. Finally, the plasma reactor is equipped with a motorized manipulator to ensure a perfect positioning of the substrate under the plasma source.

Plasma Treatment of the GO Multilayered Substrate

The multilayered structure of the GO films ensures enough mechanical and chemical stability. The pristine GO paper (GOP) is essentially designed to have carbon 83.5% -67% and oxygen 16.5% -33% respectively 83% C, 17% O is the composition of reduced graphene oxide (rGO). This With annealing composition resembles that of the chemically reduced graphene the graphene undergoes a process of reduction and its chemical composition changes in carbon 83.5%, oxygen 16.5% oxide that which is suitable structurally for bone regeneration. To provide optimal rGO thin films suitable for stem cells, its surface chemistry was modified through a plasma treatment. The substrate was then placed in the plasma reactor to graft nitrogen and oxygen based functional groups at specific plasma conditions. The plasma treatments were performed utilizing a mixture of $CH_4$ and $NH_3$ precursors in different proportions to thinly tune the amine concentration on the GOP surface. $CH_4$ and $NH_3$ precursors were varied as indicated in Table 1:

TABLE 1

| $CH_4$ (sccm) | $NH_3$ (sccm) |
| --- | --- |
| 40 | 10 |
| 30 | 20 |
| 25 | 25 |
| 20 | 30 |

Figure 3:
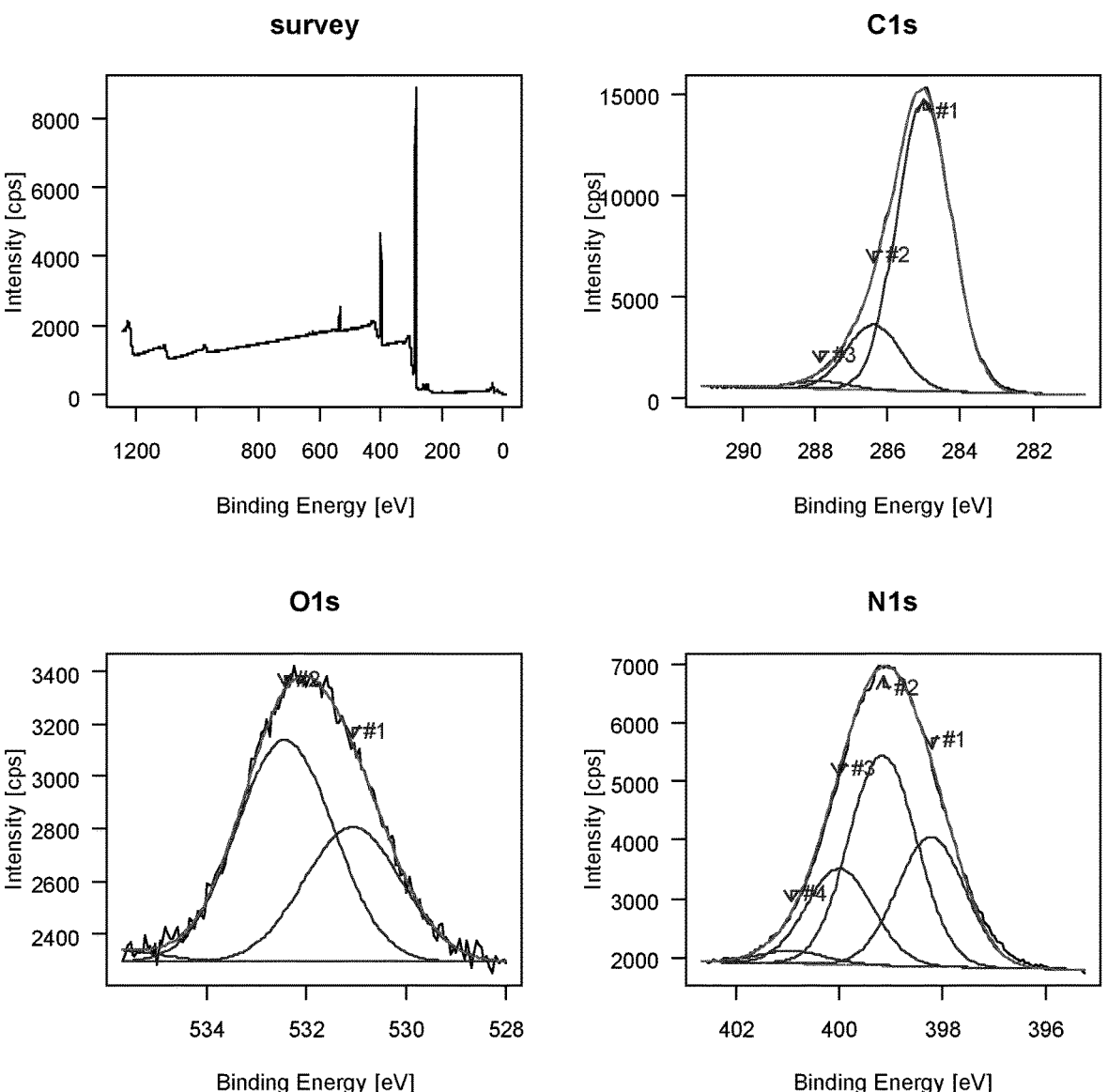
FIG. 3: example of an XPS analysis performed on the sample 30 sccm CH4 20 scc NH3—. Left to right, top to bottom are displayed a wide spectrum, the C1 s, the O1s and N1s core lines.

The pressure inside the reactor was 0.015mbar with an ion density of $\sim 10^{\wedge}12/cm^3$ thanks to the highly efficient coupling between the RF excitation power and the plasma. In these conditions the energy of the ionized species impinging the substrate surface is ~15 eV while the estimated current density at the GOP surface is 0.35 mA/cm2. We designed the plasma process to be in a quasi-neutral state meaning that it is composed by roughly the same number of ions and electrons. This allows highly efficient deposition processes even if the conductivity of the substrates is not ensured as in the case of GOP paper. The plasma treatment leads to the deposition of a very thin film which ensures stability of the materials with time and in biological environments through crosslinking of particles and monolayers connecting them both vertically and horizontally, thus ensure a crosslinking structure in all dimensions. An example of XPS analysis performed on the 30 sccm CH4 and 20 scc NH3 is shown in FIGS. 3 and 4.

As it can be seen from the wide spectrum, the intensity of the N1s core line at 400 eV binding energy is higher than that of the O1s although N1s possesses a lower sensitivity factor with respect to oxygen. In the same picture the C1s, O1s and N1s high energy resolved core lines are shown. These core lines were fitted using Gaussian components representing well tabulated chemical bonds. For any chemical bond, the stoichiometry was carefully controlled. In particular the binding energy value associated to the main peaks of the N1s core line can be associated to imine groups (component #1 at 398.2 eV), unprotonated amine groups (component #2 at 399.1 eV), protonated amine groups (components #3 and #4 at 400eV and 400.9 eV respectively) which are of paramount importance for the interaction between the substrate and the living matter ["Cell-material interactions" in Molecular and Cellular Foundations of Biomaterials—Advances in Chemical Engineering Vol. 29 Academic Press; 1 edition (Jul. 15, 2004), ISBN-10: 0120085291]

Figure 4:
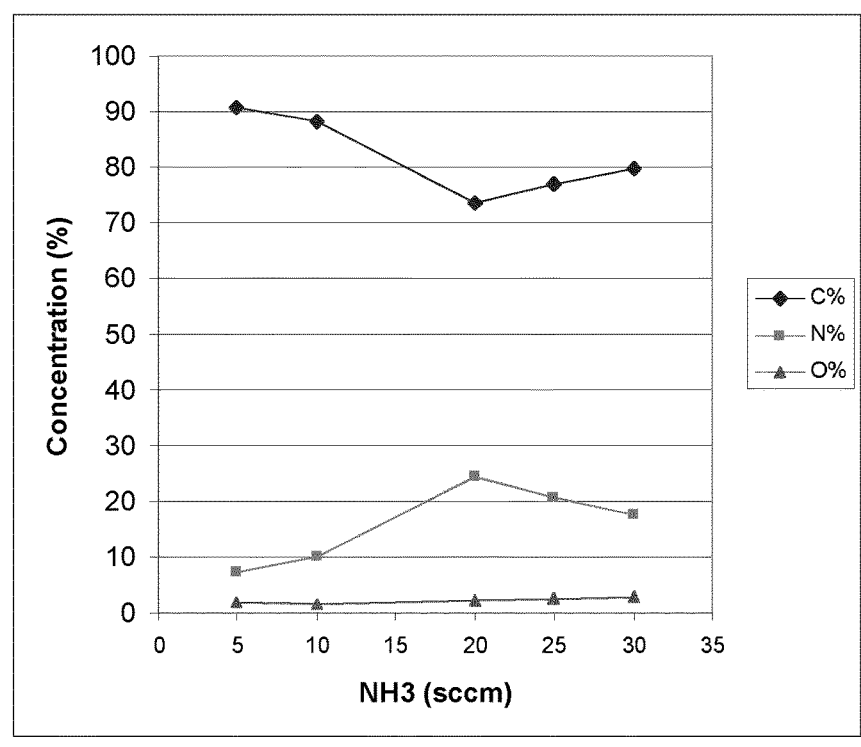
FIG. 4: trend of the carbon (blue), oxygen (red), nitrogen (green) concentration estimated by XPS on plasma treated GO paper as a function of the indicated precursor mixture

The results of the XPS analysis is summarized in the FIG. 4 where the abundance of the carbon, oxygen and nitrogen is plotted against the precursor mixture utilized to perform the plasma treatment.

The composition of the novel substrate film surfaces is significantly different than that of the pristine GOP films substrates and strictly depends on the kind of precursor mixture used and the plasma treatment conditions. In particular the oxygen concentration in the novel GO material is in the range 1.5%-2.5%. An added novelty, is the possibility to modulate the nitrogen concentration which varies form a minimum of 5-7% to a maximum of 24% which is obtained using the 30 sccm CH4, 20 sccm NH3. A further increase of the NH3 concentration in the precursor mixture leads to a reduction of the CH4 concentration thus affecting the efficiency of the film deposition and then the density of the functional groups present on the film surface. The modified GOP+thin film with the later treatment was designed to have a controllable density of polar groups towards optimal performance for the adhesion and proliferation of cells. This mainly depends on the ability to optimize the surface polarity to favour the adhesion of the extracellular matrix secreted by the cells. The macroscopic polarity of the substrate surface is the result of the interplay between the negative oxygen based polar groups (mainly COOH— and OH— groups) belonging to the GOP surface and the positively charged amine groups NH3+. A careful selection of the precursor mixture allows controlling the density of the grafted functionalities. This is are very important because they allow surface conditioning to promote cell adhesion while, at the same time, avoiding ECM protein denaturation. Finally the plasma treatment preserves the surface roughness induced by the deposition of the GOP which is a factor enabling cell adhesion and stabilization to the surface substrate. It is also important to note that we design the plasma deposition process to crosslink the graphene film and not to completely cover it and mask the graphene oxide actual effect which is utilized for the tissue regeneration and repair.

A similar work has been carried out utilizing oxygen rich gaseous precursors. As in the previous case the plasma treatment is intended to deposit a carbon film with both the properties to stabilize the graphene surface and, at the same time, providing carboxy-acid and hydroxyl functionals. It is known that different cell lines produce different extracellular matrix (ECM) proteins entering at play during the process of cell adhesion. Positively (ammonia plasma treated surfaces) and negatively (oxygen plasma treated surfaces) polarized surfaces can be selected to match the different characteristics of the ECM thus allowing optimal cell adhesion for the various kinds of cells.

Figure 5:
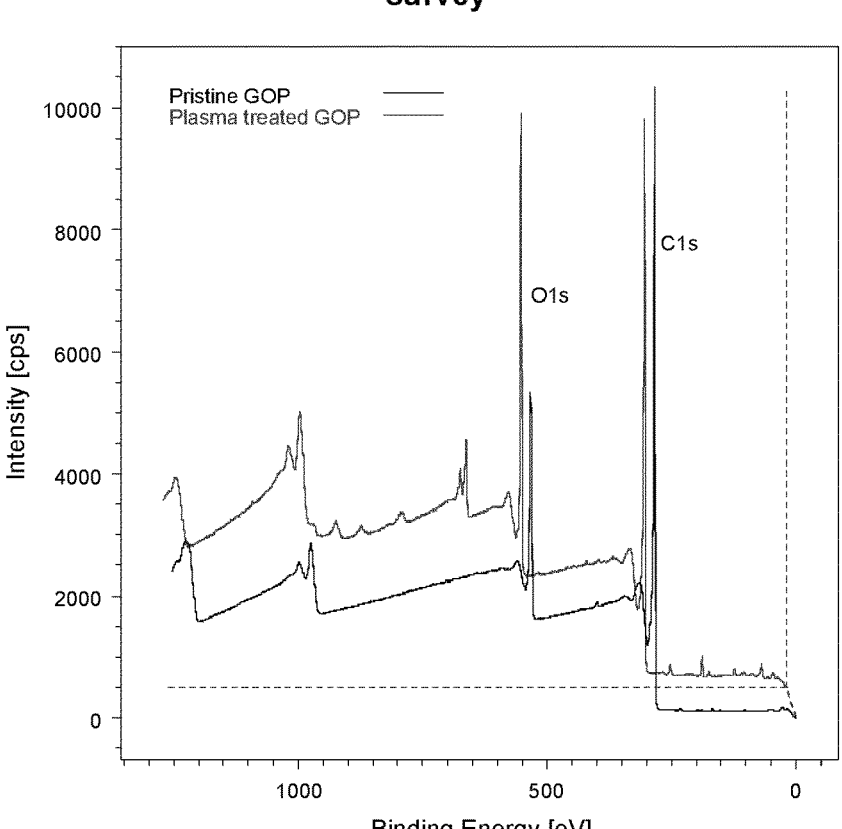
FIG. 5: wide spectra of pristine and plasma treated GO paper. A higher intensity of the O1s and lower intensity of C1s peaks in the plasma treated sample if compared with the pristine GOP testify the presence of a surface chemistry modification resulting from the deposition of the functionalized thin film.

Regarding the plasma treatments leading to negatively polarized surfaces, different percentages of pure oxygen were mixed with CH4 and introduced in the plasma reactor. As an example in the following we will describe the surface of a GO paper substrate treated introducing 20 sccm pure O2 sccm and 30 sccm CH4+30 sccm H2. The plasma source operated at 200 W for 15 min led to a deposition of a homogeneous thin film with a high density of oxygen based polar groups. In FIG. 5 are compared wide spectra from pristine and plasma treated GOP samples. Evident is the higher intensity of the oxygen peak in the plasma treated substrate with respect to that of the pristine GO paper substrate while the situation is reversed for carbon where intensity lowers with the treatment.

Figure 6:
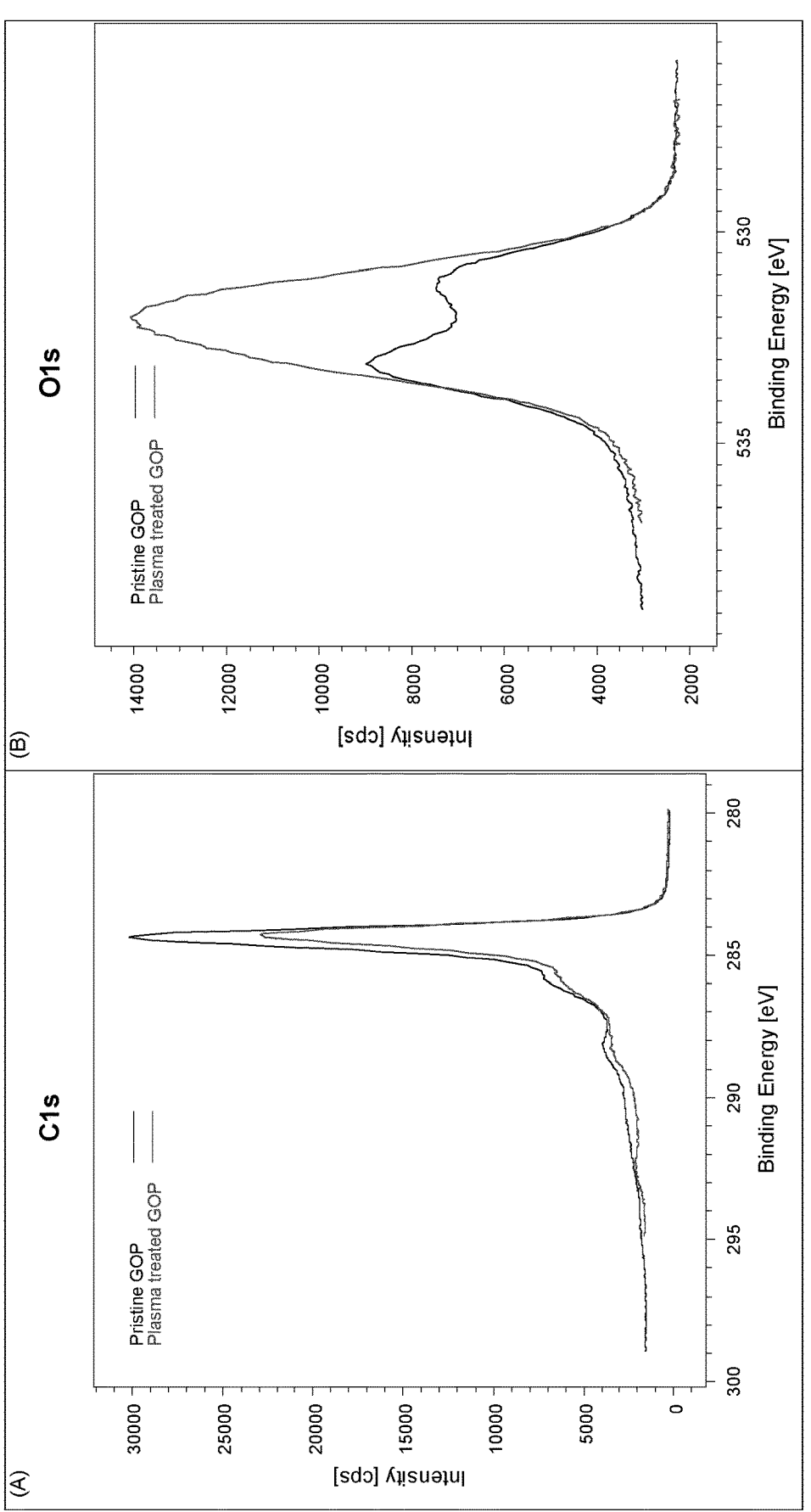
FIG. 6: comparison of the carbon (A) and oxygen (B) core lines to put in evidence changes induced by the surface plasma treatment. Peaks are normalized to a common intensity.

As for the composition of the deposited films, FIG. 6 displays both the carbon 1s and oxygen 1s core lines.

Figure 7:
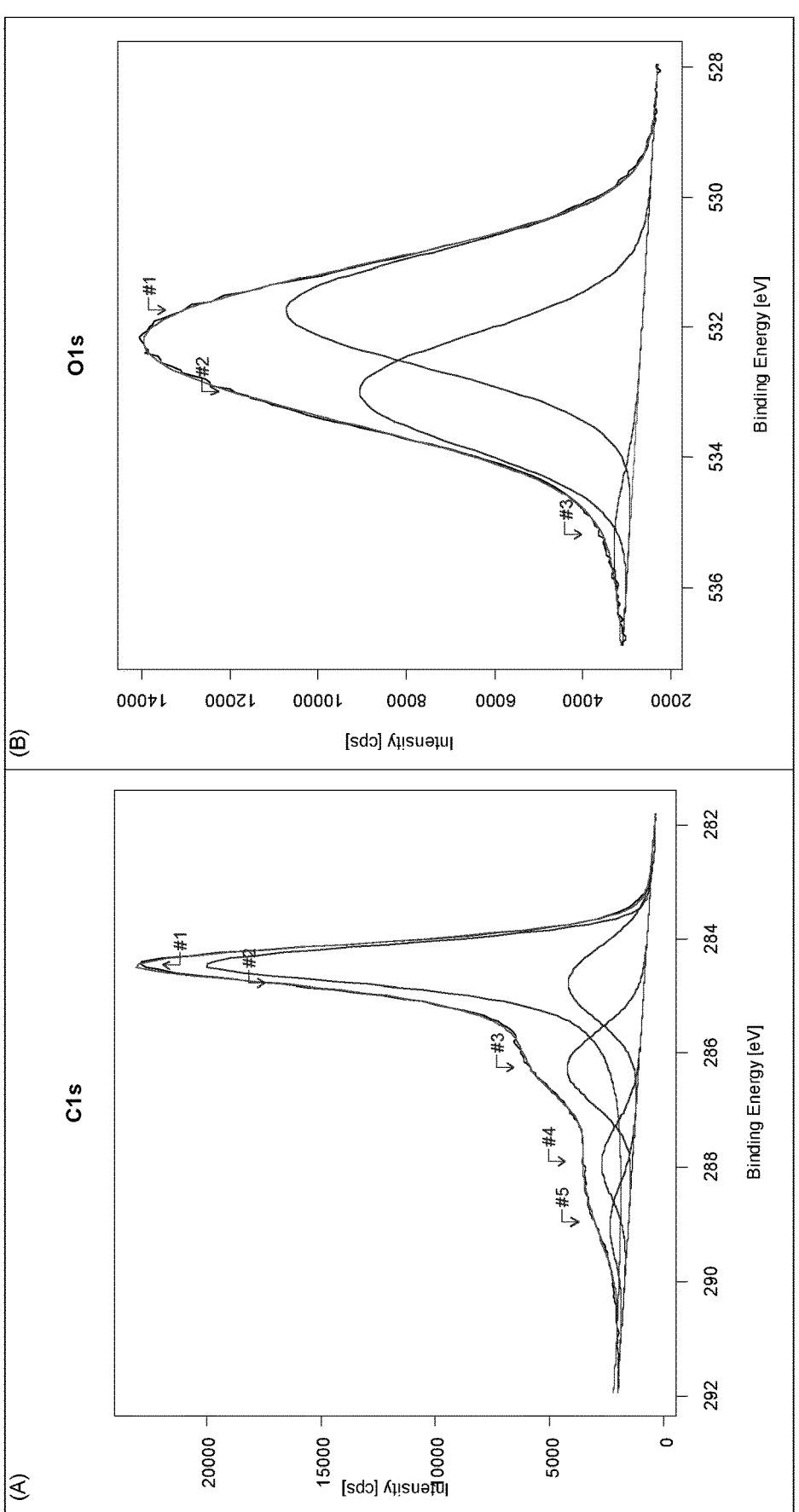
FIG. 7: an example of carbon (A) and oxygen (B) core line peak fittings. Spectra are acquired on the plasma treated GOP.

The carbon core line from the plasma treated GOP possesses similar components which are associated to hydroxy and carboxy groups with respect to the untreated GOP but a much lower intensity of the component describing the graphitic peak. Then the ratio R=[Oxidized carbon atoms/pure C atoms] is higher in the case of plasma treated GOP than in the untreated samples. More evident is the lineshape change of the oxygen core line which testifies the change of the surface chemistry occurred with the plasma treatment. The intensity of oxygen is much higher in the case of the plasma treated sample testifying the grafting of oxygen based functionals. In FIG. 7 are shown an example of peak fitting of the C1s (FIG. 7A) and O1s (FIG. 7B).

The carbon peak was fitted using 5 Gaussian components corresponding to: C1 graphitic C=C bonds at ~284.4 eV; C2 hydrocarburic CHx at 285 eV; C3 C—OH and less probable C—O—C bonds; C4 C=O bonds; C5-O—(C=O). In the case of oxygen the peaks were fitted using three components namely C1 associated to C=O bonds C2 associated to C—OH and C—O—C bonds. As underlined before, in the plasma treated samples the C1 and C2 components are much more intense which corresponds to higher concentration of C—OH, C=O, O—C—O and —O(C=O) bonds. This corresponds to a higher percentage of C atoms involved in these chemical bonds in the plasma treated GOP.

In summary, utilizing the plasma treatment we are able to thinly tune the composition of the amorphous carbon coating which can be tuned to match perfectly the chemistry required to promote cell adhesion.

In-Vitro Models Osteogenic Differentiation of MSC

Two sets of specimens were made out of each sample. One set of specimens were cultured in regular growth medium (for spontaneous differentiation) while the rest were cultured in medium containing osteogenic promoters (dexamethasone, ascorbic acid and beta-glycerophosphate) to provoke osteogenic response of ADSCs. The alkaline phosphatase activity, the calcium production and the gene expression were chosen to follow and compare the osteogenic activity under these two conditions. During the experiments, the samples were immersed in 48 culture plate and were not floating as they were maintained by inserts. The surface area of GO and glass samples were the same. Our results indicate that the soluble osteogenic promoters generally allow a better osteogenic differentiation of ADSC. However untreated GO samples and GO treated by nitrogen allowed spontaneous differentiation of ADSC into osteoblast without adding any type of osteogenic influencer in the medium comparing to glass controls of same surface cultivated in same conditions. This tremendous result is confirmed by our different tests. We also observed that calcium deposition was reached quicker on GO plane surfaces rather than GO-treated by O2 in spontaneous condition (calcium deposition and BSP2 gene expression).

Figure 8:
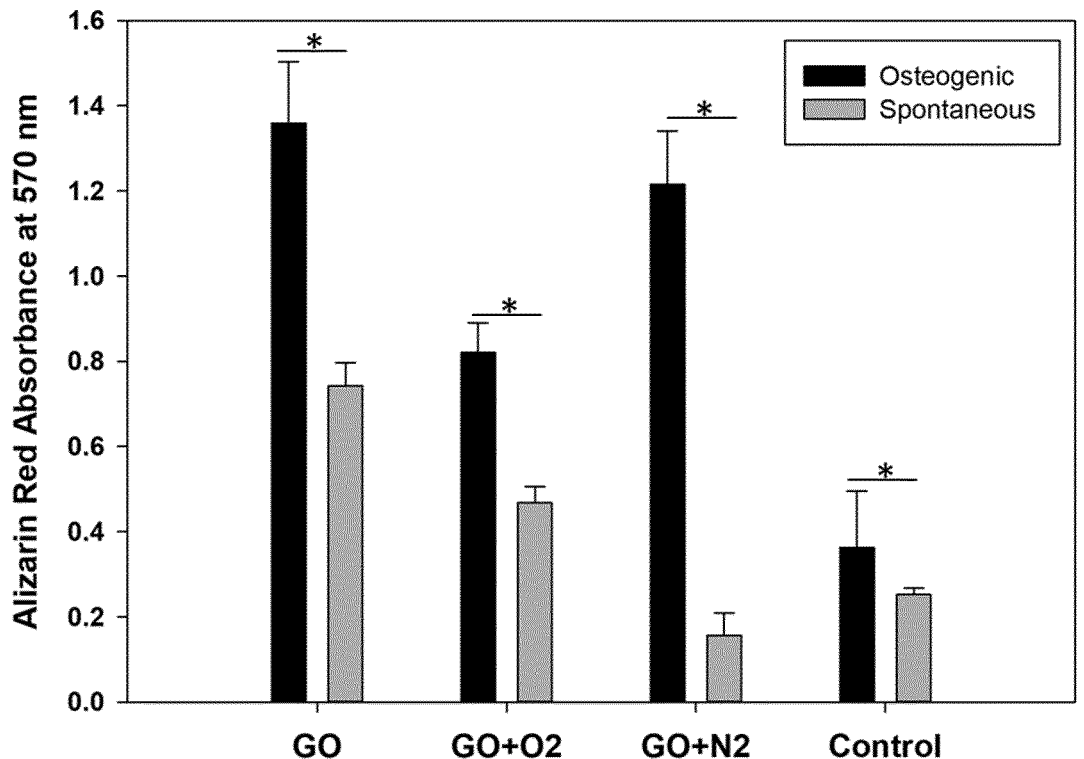
FIG. 8: Alizarin red extraction assay of ADMSCs cultured 21 days on differently GO treated films scaffolds. As control were used glass samples. Symbol * is added when difference is statistically significant (p<0.05). The samples were flat in the culture plate, maintained by inserts.

The calcium deposition was also observed quantitatively via Alizarin red staining/extraction assay at day 21 (FIG. 8). A significant increase was observed in the calcium production with osteogenic medium similarly to the results obtained with alkaline phosphase. In osteogenic conditions, the calcium production is always higher on GO non treated scaffolds (p<0.05) compared to the other samples including the control. In spontaneous conditions, we prove here that GO alone, can allow ADSC to produce 2.5 more calcic deposition than ADSC differentiated on glass. Regarding the others treatment, it seems GO alone without surface treatment provide the best surface for spontaneous differentiation of ADSC, an effect which was not described till now and proving the driving effect of GO on the differentiation of ADMSC toward the osteogenic lineage. The above results suggest that the annealed and untreated with plasma GO sample is the best candidate for the animal studies.

Figure 9:
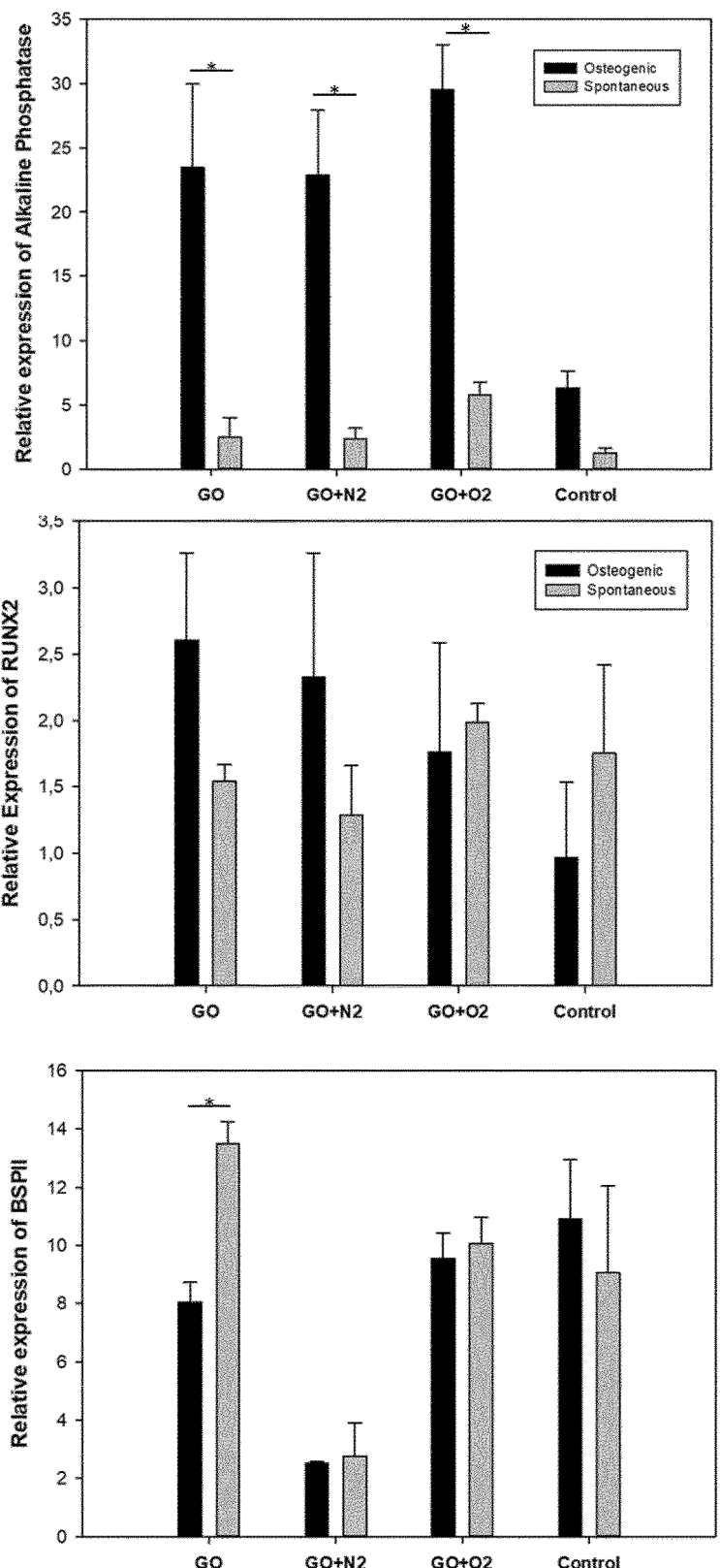
FIG. 9: Relative expression of alkaline phosphatase ALK gene, RunX2 gene and BSP2 gene of ADSC cultured for 21 days in osteogenic medium and spontaneous conditions onto differently GO treated films scaffolds. Glass samples are controls. Symbol * is added when difference is statistically significant (p<0.05). GAPDH gene was used housekeeping gene.

For the gene expression we observed the expression of three genes: alkaline phosphatase ALK, RUNX2 and bone sialioprotein BSP2. ALK and RUNX2 are supposed to be expressed at the beginning of the differentiation; BSP2 is expressed later when the calcite formation occurs. All GO treated and non-treated samples were cultivated during 21 days with glass as controls. One part of the cells was grown in "osteogenic" conditions and the other part in "spontaneous" conditions. All the results are presented FIG. 9.

In Vivo Models

Calvarial Model

Figure 10A:
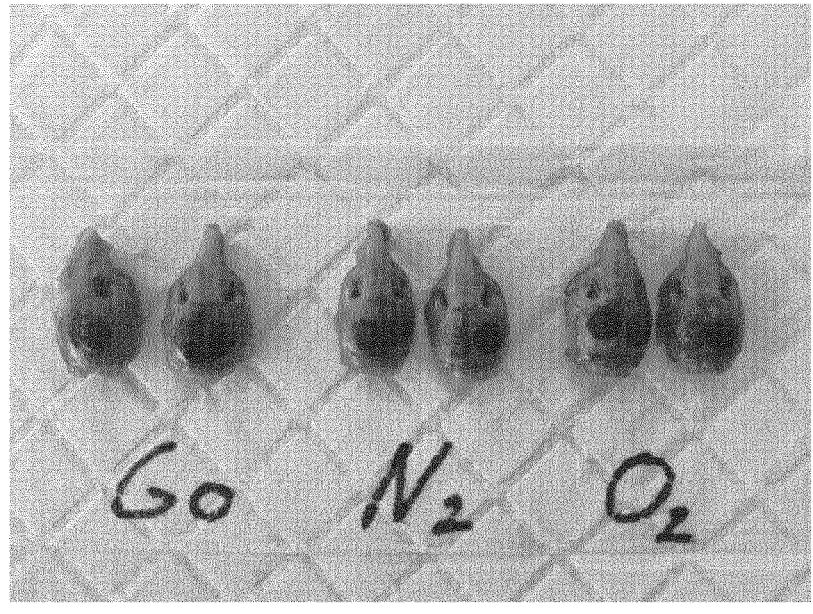
FIG. 10: (*a, b*) Critical-size calvarial defects (5 mm diameter) in mice were treated with or without GO sheets directly applied on the defect. Eight weeks after treatment, bone regeneration was measured by microCT as coverage of the defect. Data are means±SEM (n=6 per condition). ANOVA with Bonferroni post hoc test for pair-wise comparisons; *P<0.05. Representative calvarial reconstructions are shown in b. Original defect area is shaded with a red dotted outline.
Figure 10B:
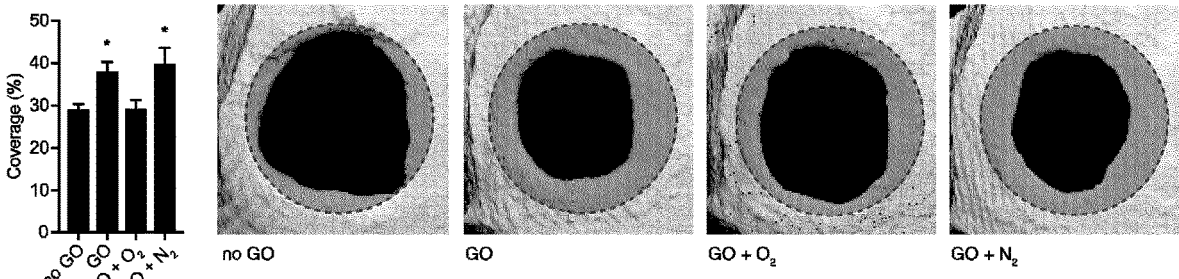
Figure 11:
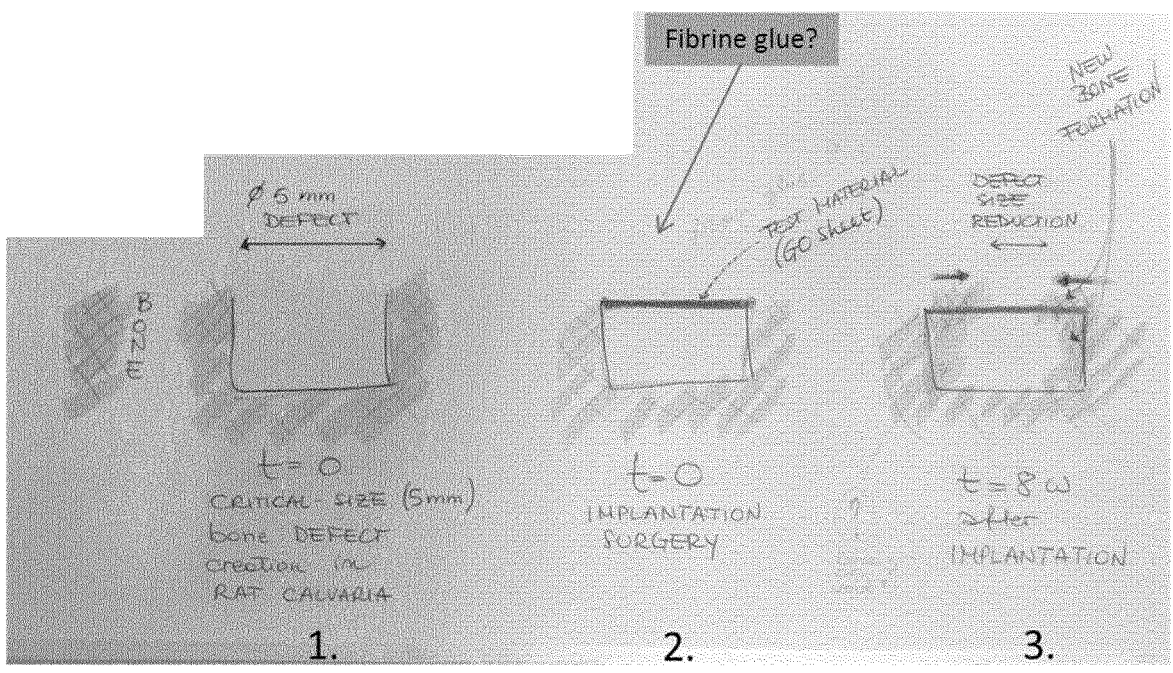
FIG. 11: Testing GO sheets in-vivo in rat calvarial critical-size bone defect model, front view (1: t=0, bone defect created in Rat calavria, 2: t=0 , implantation surgery, 3: t=8 weeks, after implantation.
Figure 12:
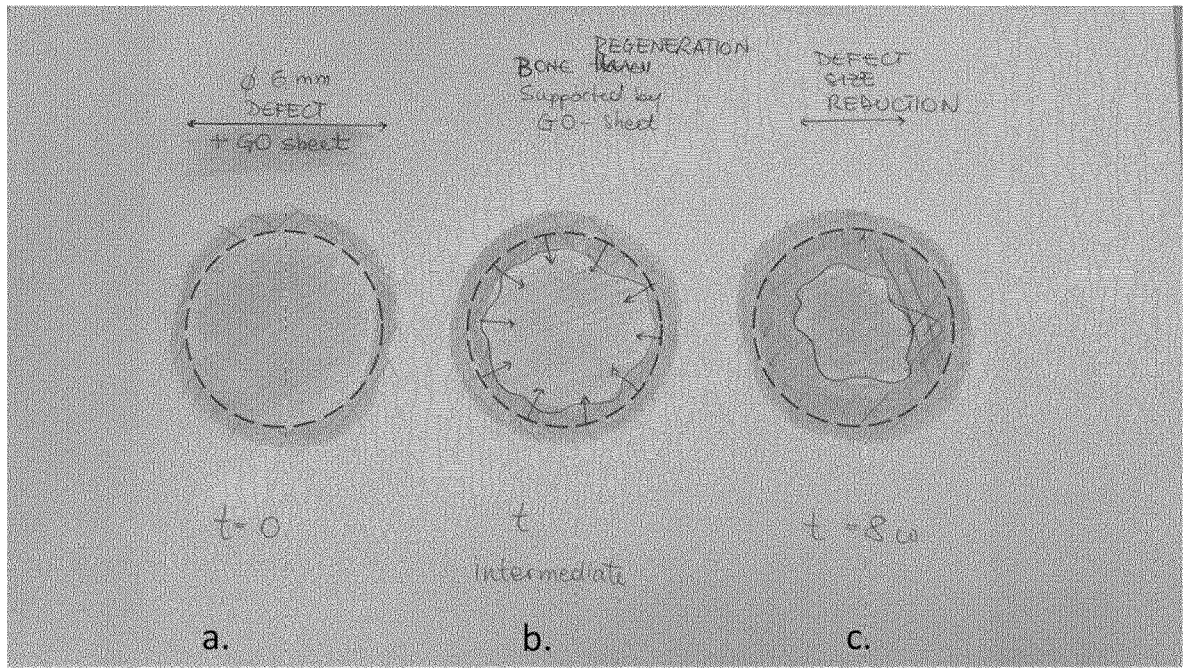
FIG. 12: Testing GO sheets in-vivo in rat calvarial critical-size bone defect model. Top view.
Figure 13A:
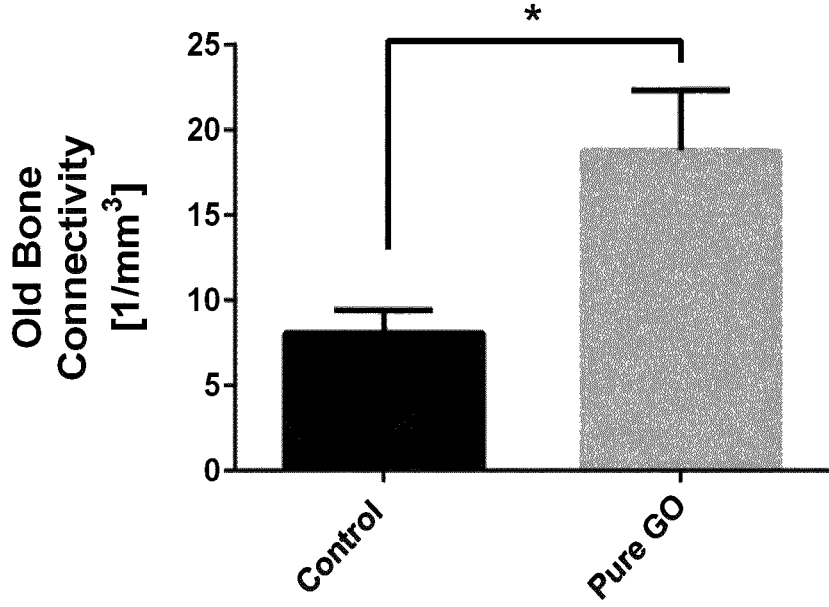
Figure 13B:
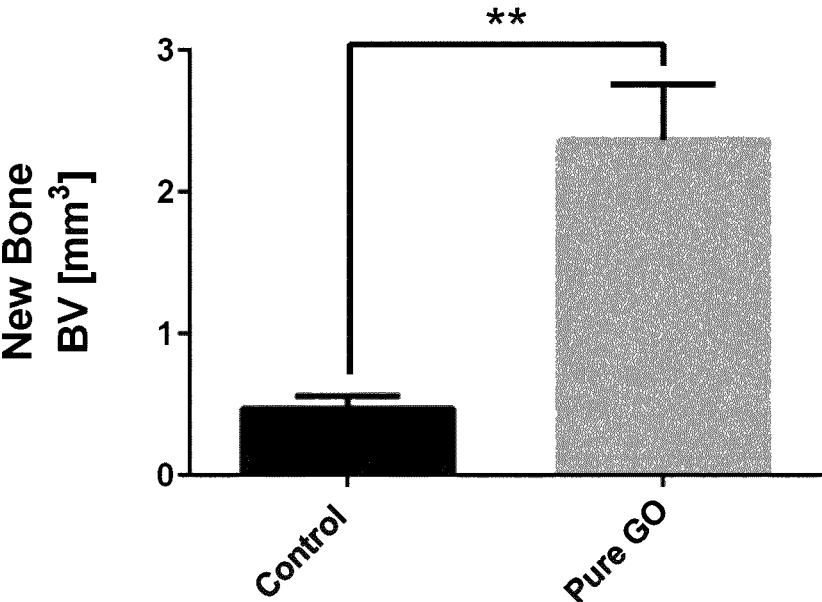
Figure 13C:
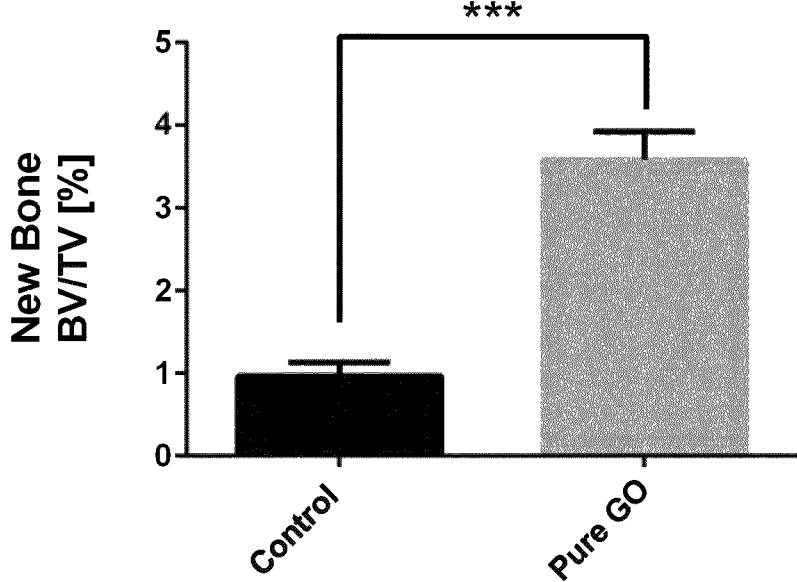
Figure 13D:
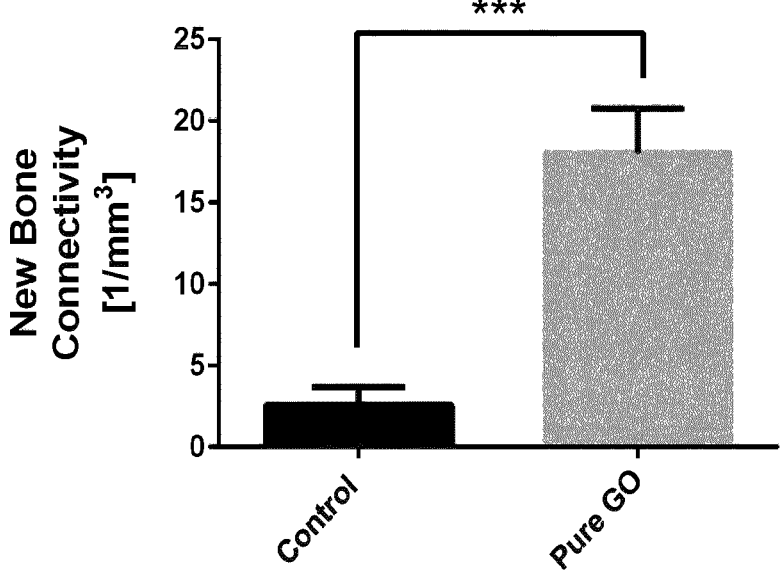

Critical-size calvarial defects (5 mm diameter) in mice were treated with the graphene sheets. Eight weeks after treatment, bone regeneration was measured by microCT as coverage of the defect. Please see FIGS. 10-12). Data are means±SEM (n≥6 per condition). ANOVA with Bonferroni post hoc test for pair-wise comparisons; *P<0.05.

2.5 MM Tibial Defect 4 weeks

Microcomputed tomography (μCT)—Segmental defect

Four weeks post-surgery, the pure GO group and the controls were assessed for the differences in old, new and total bone parameters. The total tissue volume (TV) was slightly but not significantly higher in the GO-treated than the control animals (+30%, p=0.155). While differences in parameters and trabecular properties for pre-existing and highly mineralized new bone tissue were mostly negligible (BVh, BVh/TV, TbN, Tb.Th), a significant elevation of 134% in Conn.D was observed. Importantly, we found a dramatic 4-fold increase in the volume of low radio-opacity bone tissue (BVl, mainly newly formed bone), which consisted of a 2.8-fold increase when related to the slightly elevated TV (BVl/TV). This increase in bone mass was associated with a significant 36% increase in Tb.Th and 20% non-significant increase in Tb.N. We also observed a 6-fold increase in Conn.D, which suggests a vast enhancement of the biomechanical properties of the newly formed bone, please see FIGS. 13-17).

Graphene Oxide Bone Regeneration

GO Increased Blood Fusion

Bone generally takes six to 12 weeks to heal to a significant degree. There are multiple factors that could influence healing time including the location and severity of the fracture. There are three main healing stages including inflammation, bone production and bone remodelling. The inflammation stage takes several days and it it's a consequence of the bleeding into the area that occur after fracture and also result in blood clotting. Since GO was applied immediately, the effect was further accelerated. Since GO also have angiogenesis potential (as explained in the following section.

GO Increased the Rate and Amount of Callus Production

The initial stage of bone production and regeneration, following the inflammation stage, is the production of the soft callus. The soft callus is basically a fibrous tissue and cartilage, see Figure XX, that progress into hard bone (or hard callus). This process takes several weeks to complete. Significant connective tissue was observed in the GO sample. The fact that the callus is so obviously noticed after 4 weeks which is early compared to regular appearance which takes longer in the untreated samples.

GO and Bone Remodeling

Bone remodeling will take several months to complete with bone becoming compact and return to original shape. Its important for blood circulation in the area to improve and GO here plays a continuous role since the degradation of GO implant is slower than this stage. Signs of bone remodeling were observed in the GO treated samples in 4 weeks only despite the fact that bone remodeling takes months to remodel

Energy Storage Application

Graphene oxide material is produced starting from graphene oxide flakes, which is a material that is relatively cheap and considerably cheaper than Graphene. There are many suppliers of Graphene Oxide powder (e.g. Graphenea, ACS), with typical prices around $400/kg. Graphene Oxide nano flakes are converted into thin sheets of reduced graphene oxide (RGO) through sonication, drying and thermal treatments (similar to the steps described above). The RGO sheets are then modified further through multi steps process of thermal cycling and plasma treatments to create a mechanically strong thin sheets of Graphene material (MGO) with superior electrical functionality (see FIG. 18).

The processing steps include a series of thermal treatments to infuse the graphene oxide nano flakes to create a sheet or film like material. Then further thermal process is carried out at a specific temperature and time that enables the reduction of oxygen in a way that increases the sheet ability to store electrons (energy). A plasma treatment process is followed using different concentrations of methane and hydrogen gases to create stability in the structure and induce crosslinks between the reduced graphene layers. The plasma treatment process is repeated, but using only hydrogen gas, in order to reduce the oxygen even further from the structure to increase electron storage capacity (FIG. 2).

The MGO material of the invention has been put through systematic electrochemical evaluation using cyclic voltammetry, galvanostatic charge—discharge and electrochemical impedance spectroscopy. The results strongly indicate that the graphene oxide material of the invention stores energy many orders of magnitude more than supercapacitors on the market (see FIG. 20) while delivering high power. Additionally, MGO can store energy as well as the best fuel cell on the market with the potential benefit of significantly more power density. MGO also shows optimum charge-discharge performance with significantly better longevity and stability compared with the best batteries on the market. MGO material is also potentially lower in cost. Energy storage products made with our novel modified graphene materials would have a very small environmental footprint as the electrostatic capacitor and the battery, could be made from different variations of our modified graphene material which is completely recyclable.

Electrochemistry Evaluations

Electrochemistry evaluations were conducted on a range of samples of our MGO sheets. These samples were synthesized with the basic treatments that we used to produce the conducting sheets in the cheapest way. There are many possibilities to upgrade the modification process with more sophisticated stages to produce a more refined MGO product. This enables the MGO technology to work as a platform with the capability to customise the end product with different capabilities/properties for particular application e.g. types of supercapacitors or different energy storage devices like fuel cells or batteries. Possible process extensions include the addition of chemical reduction, freeze drying and thermal cycling to produce even thinner sheets (<5 micrometers).

Chronoamperometric characterizations were conducted on multiple MGO samples by subjecting them to a given potential (charging), followed by a standard discharging process. This process allows for monitoring the current density of both processes and calculates the amount of charge that is loaded and released. FIG. 19 shows the values of charge that is (A) loaded and (B) released from fully charged MGO samples in 80 seconds. Most samples discharged by 50% of its capacity in 80 seconds indicating significant discharge power. The charging power was twice as fast as the discharge power. This charging/discharging behavior demonstrated by MGO material of the invention (basic treatment) is favourable to the operations of batteries. Alternative structural modification of the MGO material, such as increasing crosslinking density, would yield different behaviour suiting the operation of supercapacitors or fuel cells.

Figure 20:
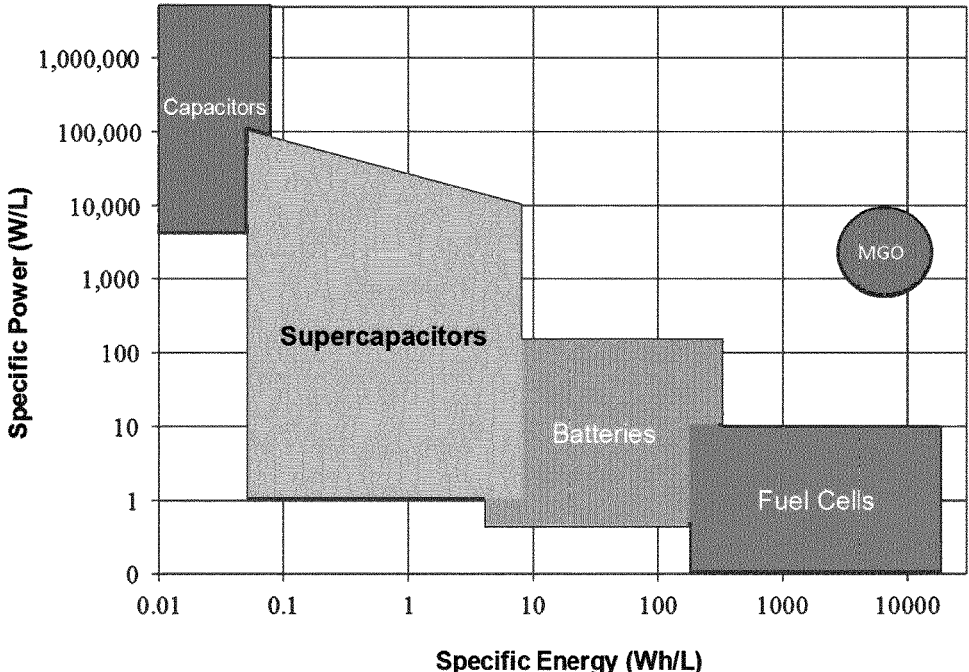

An All-Graphene Battery solving the Energy Storage Trilemma is needed by the device market. AGBEV will address this gap by developing the MGO Materials Platform towards a specific application. FIG. 20 presents the key energy storage devices in the power vs. energy plane. The specific power and energy values for our MGO samples are summarised and used to construct the specified MGO area (Figure , red circle on right, on a logarithmic scale). Our MGO Materials Platform has very high specific energy and power that can provide significant performance improvements to these energy storage devices: extending the performances of Supercapacitors, Batteries and Fuel Cells to the MGO arena.

Equivalents

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A method of producing a multi-layered functionalised graphene oxide material, comprising the steps of:
   providing an aqueous suspension of graphene oxide flakes;
   size reducing the graphene oxide flakes in the suspension to provide an aqueous suspension of particulate graphene oxide having an average particle size of less than 1 μm;
   drying the aqueous suspension in a vessel to provide a multi-layered graphene oxide material;
   annealing the multi-layered graphene oxide material to provide a multi-layered reduced graphene oxide material; and
   surface grafting functional groups to the surface of the multi-layered graphene oxide material by reacting the multi-layered reduced graphene oxide material with a functional group precursor in the presence of plasma to provide a multi-layered functionalized graphene oxide material, wherein the functional group precursor includes an alkane and (a) oxygen or (b) a precursor of an amine functional group.

2. A method according to claim 1, in which the multi-layered functionalised graphene oxide material comprises at least 100 layers.

3. A method according to claim 1 in which the annealing step is configured to provide a multi-layered reduced graphene oxide material with an oxygen concentration of 10-25%.

4. A method according to claim 1, in which the surface grafting step is configured to provide a multi-layered functionalised graphene oxide material with an oxygen concentration of about 4-6%.

5. A method according to claim 1, in which the multi-layered functionalised graphene oxide material has a thickness of about 1-10 microns.

6. A method according to claim 1, in which the multi-layered functionalised graphene oxide material has a thickness of about 1-5 microns.

7. A method according to claim 1, in which the aqueous suspension of particulate graphene oxide is dried to provide the multi-layered reduced graphene oxide material as a thin sheet having a thickness of less than 1 um.

8. A method according to claim 1, in which the functional group precursor includes hydrogen.

9. A method according to claim 1, in which the plasma is non-thermal low-pressure plasma afterglow.

10. A method according to claim 1, in which the suspension of graphene oxide flakes is obtained by exfoliation of crystalline graphite in a concentrated sulphuric acid solution.

11. A method according to claim 1, in which the graphene oxide flakes in the suspension are size reduced by a process of sonication.

12. A method according to claim 1, in which the aqueous suspension employed in the drying step has a concentration of particulate graphene oxide of 1 to 10 mg/ml.

13. A method according to claim 1, in which the annealing step is performed at a temperature of 150-250° C.

14. A method according to claim 1, in which the drying and annealing steps are configured to provide multi-layered reduced graphene oxide material having a stiffness of 20-40 GPa.

15. A method of producing a multi-layered functionalised graphene oxide material, comprising the steps of:
   providing an aqueous suspension of graphene oxide flakes;
   size reducing the graphene oxide flakes in the suspension to provide an aqueous suspension of particulate graphene oxide having an average particle size of less than 1 μm;
   drying the aqueous suspension in a vessel to provide a multi-layered graphene oxide material;
   annealing the multi-layered graphene oxide material to provide a multi-layered reduced graphene oxide material; and
   surface grafting functional groups to the surface of the multi-layered reduced graphene oxide material by reacting the multi-layered reduced graphene oxide material with at least two functional group precursors in the presence of plasma, to provide a multi-layered functionalized graphene oxide material,
wherein the at least two functional group precursors comprise an alkane and oxygen.

16. A method of producing a multi-layered functionalised graphene oxide material, comprising the steps of:
   providing an aqueous suspension of graphene oxide flakes;
   size reducing the graphene oxide flakes in the suspension to provide an aqueous suspension of particulate graphene oxide having an average particle size of less than 1 μm;
   drying the aqueous suspension in a vessel to provide a multi-layered graphene oxide material;
   annealing the multi-layered graphene oxide material to provide a multi-layered reduced graphene oxide material; and
   surface grafting functional groups to the surface of the multi-layered reduced graphene oxide material by reacting the multi-layered reduced graphene oxide material with at least two functional group precursors in the presence of plasma, to provide a multi-layered functionalized graphene oxide material,
wherein the at least two functional group precursors comprise an alkane and a precursor of an amine functional group.

* * * * *